United States Patent
Osorio et al.

(10) Patent No.: US 9,314,633 B2
(45) Date of Patent: Apr. 19, 2016

(54) CONTINGENT CARDIO-PROTECTION FOR EPILEPSY PATIENTS

(75) Inventors: Ivan Osorio, Leawood, KS (US); Timothy L. Scott, Sugar Land, TX (US)

(73) Assignees: CYBERONICS, INC., Houston, TX (US); FLINT HILLS SCIENTIFIC LLC, Lawrence, KS (US)

(*) Notice: Subject to any disclaimer, the term of this patent is extended or adjusted under 35 U.S.C. 154(b) by 507 days.

(21) Appl. No.: 13/601,099

(22) Filed: Aug. 31, 2012

(65) Prior Publication Data

US 2012/0330369 A1    Dec. 27, 2012

Related U.S. Application Data

(63) Continuation-in-part of application No. 12/020,097, filed on Jan. 25, 2008, now Pat. No. 8,565,867, and a continuation-in-part of application No. 12/020,195, filed on Jan. 25, 2008, now Pat. No. 8,260,426.

(51) Int. Cl.
*A61N 1/36* (2006.01)
*A61N 1/05* (2006.01)

(52) U.S. Cl.
CPC ........ *A61N 1/36185* (2013.01); *A61N 1/36064* (2013.01); *A61N 1/0556* (2013.01); *A61N 1/36114* (2013.01); *A61N 1/36117* (2013.01)

(58) Field of Classification Search
CPC ............ A61N 1/0556; A61N 1/36064; A61N 1/36114; A61N 1/36117; A61N 1/36185
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |

(Continued)

FOREIGN PATENT DOCUMENTS

| | | |
|---|---|---|
| CA | 2339971 | 6/2004 |
| EP | 0402683 | 12/1990 |

(Continued)

OTHER PUBLICATIONS

International Application No. PCT/US2013/056209, International Search Report and Written Opinion dated Nov. 19, 2013, 14 pages.

(Continued)

*Primary Examiner* — Amanda Patton

(57) ABSTRACT

Disclosed are methods and systems for treating epilepsy by stimulating a main trunk of a vagus nerve, or a left vagus nerve, when the patient has had no seizure or a seizure that is not characterized by cardiac changes such as an increase in heart rate, and stimulating a cardiac branch of a vagus nerve, or a right vagus nerve, when the patient has had a seizure characterized by cardiac changes such as a heart rate increase.

20 Claims, 7 Drawing Sheets

(56) References Cited

U.S. PATENT DOCUMENTS

| | | |
|---|---|---|
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 5,025,807 A | 6/1991 | Zabara |
| 5,081,987 A | 1/1992 | Nigam |
| 5,154,172 A | 10/1992 | Terry, Jr. et al. |
| 5,179,950 A | 1/1993 | Stanislaw |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,531,778 A | 7/1996 | Maschino et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Dorfmeister et al. |
| 6,002,966 A | 12/1999 | Loeb et al. |
| 6,016,449 A | 1/2000 | Fischell et al. |
| 6,041,258 A | 3/2000 | Cigaina et al. |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,295,472 B1 | 9/2001 | Rubenstein et al. |
| 6,304,775 B1 | 10/2001 | Iasemidis et al. |
| 6,308,102 B1 | 10/2001 | Sieracki |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja et al. |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,600,955 B1 | 7/2003 | Zierhofer |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |

(56) References Cited

U.S. PATENT DOCUMENTS

| | | |
|---|---|---|
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Sypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0040774 A1 | 2/2003 | Terry, Jr. et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak, III |
| 2003/0181959 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathurs |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |

(56) References Cited

U.S. PATENT DOCUMENTS

| | | |
|---|---|---|
| 2005/0119703 A1 | 6/2005 | DiLorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby, Jr. et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja et al. |
| 2006/0015153 A1 | 1/2006 | Gliner et al. |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0156179 A1 | 1/2007 | Bertolotti et al. |
| 2007/0027486 A1 | 2/2007 | Armstrong |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073346 A1 | 3/2007 | Corbucci et al. |
| 2007/0073355 A1 | 3/2007 | Dilorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson et al. |
| 2007/0100278 A1 | 5/2007 | Frei et al. |
| 2007/0100397 A1 | 5/2007 | Seeberger et al. |
| 2007/0100398 A1 | 5/2007 | Sload |
| 2007/0112393 A1 | 5/2007 | Gliner et al. |
| 2007/0123946 A1 | 5/2007 | Masoud |
| 2007/0135855 A1 | 6/2007 | Foshee et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | Dilorenzo et al. |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179558 A1 | 8/2007 | Gliner et al. |
| 2007/0191905 A1 | 8/2007 | Errico et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0233193 A1 | 10/2007 | Craig |
| 2007/0233194 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0255147 A1 | 11/2007 | Drew et al. |
| 2007/0255155 A1 | 11/2007 | Drew et al. |
| 2007/0255330 A1 | 11/2007 | Lee et al. |

(56) References Cited

U.S. PATENT DOCUMENTS

| | | |
|---|---|---|
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0076567 A1 | 3/2009 | Fowler et al. |
| 2009/0192567 A1 | 7/2009 | Armstrong et al. |

FOREIGN PATENT DOCUMENTS

| | | |
|---|---|---|
| EP | 0713714 | 5/1996 |
| EP | 1139861 B1 | 12/1999 |
| EP | 1070518 | 1/2001 |
| EP | 0944411 B1 | 4/2001 |
| EP | 1145736 A2 | 10/2001 |
| EP | 1483020 | 12/2004 |
| EP | 1486232 A2 | 12/2004 |
| EP | 1595497 A1 | 11/2005 |
| EP | 1120130 | 12/2005 |
| EP | 1647300 A3 | 4/2006 |
| EP | 1202775 B1 | 9/2006 |
| GB | 2026870 A | 2/1980 |
| GB | 2079610 A | 1/1982 |
| WO | 9302744 | 2/1993 |
| WO | 9417771 | 8/1994 |
| WO | 0064336 A1 | 11/2000 |
| WO | 0108749 | 2/2001 |
| WO | 03085546 | 10/2003 |
| WO | 2004036377 A2 | 4/2004 |
| WO | 2004064918 | 8/2004 |
| WO | 2004069330 | 8/2004 |
| WO | 2004071575 | 8/2004 |
| WO | 2004075982 | 9/2004 |
| WO | 2004112894 | 12/2004 |
| WO | 2005007120 A2 | 1/2005 |
| WO | 2005007232 | 1/2005 |
| WO | 2005053788 A1 | 6/2005 |
| WO | 2005028026 | 7/2005 |
| WO | 2005067599 A2 | 7/2005 |
| WO | 2005101282 | 10/2005 |
| WO | 2006014760 | 2/2006 |
| WO | 2006019822 | 2/2006 |
| WO | 2006050144 A1 | 5/2006 |
| WO | 2006122148 A2 | 11/2006 |
| WO | 2007018793 A1 | 2/2007 |
| WO | 2007066343 A2 | 6/2007 |
| WO | 2007072425 A2 | 6/2007 |
| WO | 2007124126 A2 | 11/2007 |
| WO | 2007124190 A2 | 11/2007 |
| WO | 2007124192 A1 | 11/2007 |
| WO | 2007142523 A1 | 12/2007 |

OTHER PUBLICATIONS

Bachman, D. et al., "Effects of Vagal Volleys and Serotonin on Units of Cingulate Cortex in Monkeys", Brain Research, vol. 130, 1977, pp. 253-269.

Bohning, D.E., et al.; "Feasibility of Vagus Nerve Stimulation—Synchronized Blood Oxygenation Level-Dependent Functional MRI;" A Journal of Clinical and Laboratory Research: Investigative Radiology; vol. 36, No. 8 (Aug. 2001 ); pp. 470-479.

Boon, P. et al., "Programmed and Magnet-Induced Vagus Nerve Stimulation for Refractory Epilepsy", Journal of Clinical Neurophysiology, vol. 18, No. 5, 2001, p. 402-407.

Clark, K. et al., "Posttraining Electrical Stimulation of Vagal Afferents with Concomitant Vagal Efferent Inactivation Enhances Memory Storage Processes in the Rat", Neurobiology of Learning and Memory, vol. 70, Article No. NL983863, 1998, pp. 364-373.

Clark, K. B., et al.; "Enhanced Recognition Memory Following Vagus Nerve Stimulation in Human Subjects;" Nature Neuroscience, vol. 2, No. 1, (Jan. 1999). pp.93-98.

Craig, a.D. (BUD); "Distribution of Trigeminothalamic and Spinothalamic Lamina I Terminations in the Macaque Monkey;" the Journal of Comparative Neurology, vol. 477, pp. 119-148 (2004).

DeGiorgo, Christopher M., et al.; "Vagus Nerve Stimulation: Analysis of Device Parameters in 1 54 Patients During the Long-Term XE5 Study;" Epilepsia, vol. 42, No. 8; pp. 1017-1020 (2001).

Devous, Michael D., et al.; "Effects of Vagus Nerve Stimulation on Regional Cerebral Blood Flow in Treatment- Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Dodrill, PhD., et al.; "Effects of Vagal Nerve Stimulation on Cognition and Quality of Life in Epilepsy;" Epilepsy and Behavior, vol. 2 (2001 ); pp. 46-53.

Fanselow, E.E., at al.; "Reduction of Pentylenetetrazole-Induced Seizure Activity in Awake Rates by Seizure- Triggered Trigeminal Nerve Stimulation;" The Journal of Neuroscience, Nov. 1, 2000; vol. 20/21; pp. 8160-8168.

Fromes, G. A. et al.; "Clinical Utility of On-Demand Magnet use with Vagus Nerve Stimulation;" AES Proceedings, p. 117.

(56) References Cited

OTHER PUBLICATIONS

George, M.S., et al.; "Open Trial of VNS Therapy in Severe Anxiety Disorders;" 156th American Psychiatric Association Annual Meeting; May 17-22, 2003.

George, M. et al., "Vagus Nerve Stimulation: A New Tool for Brain Research and Therapy", Society of Biological Psychiatry, vol. 47, 2000, pp. 287-295.

Hallowitz, R. et al., "Effects of Vagal Volleys on Units of Intralaminar and Juxtalaminar Thalamic Nuclei in Monkeys", Brain Research, vol. 130, No. 2, Jul. 1977, pp. 271-286.

Harry, J.D., et al.; "Balancing Act: Noise is the Key to Restoring the Body's Sense of Equilibrium;" IEEE Spectrum (Apr. 2005) pp. 37-41.

Henry, T., "Therapeutic Mechanisms of Vague Name Stimulation", Neurology, vol. 59 (Supp. 4), Sep. 2002, pp. S3-S14.

Henry, T. R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

King, M.D., "Effects of Short-Term Vagus Nerve Stimulation (VNS) on FOS Expression in Rat Brain Nuclei" 58th Annual Scientific Convention of the Society of Biological Psychiatry, (May, 2003).

Klapper, MD., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes with Vagus Nerve Stimulation", Journal of Clinical Neurophysiology, vol. 18, No. 5, Sep. 2001, pp. 434-441.

Labar, D., "Vagus Nerve Stimulation for 1 Year in 269 patients on Unchanged Antiepilectic Drugs" Seizure vol. 13, (2004) pp. 392-398.

Liebman, K. M. et al.; "Improvement in Cognitive Function After Vagal Nerve Stimulator Implantation;" Epilepsia, vol. 39, Suppl. 6 (1998) 1 page.

Lockard, J. et al., "Feasibility and safety of vagal stimulation in monkey model", Epilepsia, vol. 31 (Supp. 2), 1990, pp. S20-S26.

Malow, Ba, et al.; "Vagus Nerve Stimulation Reduces Daytime Sleepiness in Epilepsy Patients" Neurology 57 (2001) pp. 879-884.

McClintock, P., "Can Noise Actually Boost Brain Power", Physics World, Jul. 2002, vol. 15, pp. 20-21.

Mori, T. et al., "Noise-Induced Entrainment and Stochastic Resonance in Human Brain Waves", Physical Review Letters, vol. 88, No. 21, 2002, pp. 218101-1-2180101-4.

Rugg-Gunn, F.J., et al.; "Cardiac Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents," IEEE Transactions on Biomedical Engineering, vol. 45, No. 8 (Aug. 1998) pp. 1 044-1 050.

Schachter, S.C., et al.; "Progress in Epilepsy Research: Vagus Nerve Stimulation," Epilepsia, vol. 39, No. 7 (1998) pp. 677-686.

Tatum, W.O., et al.; "Ventricular Asystole During Vagus Nerve Stimulation for Epilepsy in Humans" American Academy of Neuologgy (1999) p. 1267 (See also pp. 1 1 17, 1 166, and 1 265).

Tatum, W.O., et al.; "Vagus Nerve Stimulation and Drug Reduction" Neurology, vol. 56, No. 4 (Feb. 2001) pp. 561-563.

Terry, R. et al., "The Implantable Neurocybernetic Prosthesis System", Pacing and Clinical Electrophysiology, vol. 14, No. 1, Jan. 1991, pp. 86-93.

Tubbs, R. et al., "Left-Sided Vagus Nerve Stimulation Decreases Intracranial Pressure Without Resultant Bradycardia in the Pig: A Potential Therapeutic Modality for Humans", Child's Nervous System, vol. 20, No. 5, May 2004, pp. 309-312.

Valdez-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 1 13-1 18.

Vonck, K. et al., "The Mechanism of Action of Vagus Nerve Stimulation for Refractory Epilepsy—The Current Status", Journal of Neurophysiology, vol. 18, No. 5, 2001, pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Woodbury, J. et al., "Vagal stimulation reduces the severity of maximal electroshock seizures in intact rats: use of a cuff electrode for stimulating and recording", Pacing and Clinical Electrophysiology, vol. 14, Jan. 1991, pp. 94-107.

Zabara, J., "Inhibition of Experimental Seizures in Canines by Repetitive Vagal Stimulation", Epilepsia, vol. 33, No. 6, 1992, pp. 1005-1012.

CONTINGENT CARDIO-PROTECTION FOR EPILEPSY PATIENTS

CROSS-REFERENCE TO RELATED APPLICATIONS

This application is a continuation-in-part of and claims priority to U.S. patent application Ser. No. 12/020,097 filed Jan. 25, 2008 and U.S. patent application Ser. No. 12/020,195 filed Jan. 25, 2008, both of which are incorporated herein by reference in their entirety.

BACKGROUND OF THE INVENTION

This invention relates generally to medical devices, and, more particularly, to methods, apparatus, and systems for performing vagus nerve stimulation (VNS) for treating epileptic seizures characterized by cardiac changes, including ictal tachycardia.

DESCRIPTION OF THE RELATED ART

While seizures are the best known and most studied manifestations of epilepsy, cardiac alterations are prevalent and may account for the high rate of sudden unexpected death (SUDEP) in these patients. These alterations may include changes in rate (most commonly tachycardia, rarely bradycardia or asystole), rhythm (PACs, PVCs,), conduction (e.g., bundle branch block) and repolarization abnormalities (e.g., Q-T prolongation, which occurs primarily during (ictal) but also between (inter-ictal) seizures). In addition, S-T segment depression (a sign of myocardial ischemia) is observed during epileptic seizures. Significant elevations in heart-type fatty acid binding protein (H-FABP), a cytoplasmic low-molecular weight protein released into the circulation during myocardial injury have been documented in patients with epilepsy and without evidence of coronary artery disease, not only during seizures but also during free-seizure periods. H-FABP is a more sensitive and specific marker of myocardial ischemia than troponin I or CK-MB. Elevations in H-FABP appear to be un-correlated with duration of illness, of the recorded seizures, or with the Chalfont severity score of the patients.

The cardiac alterations in epilepsy patients, both during and between seizures, have a multi-factorial etiology, but a vago-sympathetic imbalance seems to play a prominent role in their generation. The majority of epileptic seizures enhance the sympathetic tone (plasma noradrenaline and adrenaline rise markedly after seizure onset) causing tachycardia, arterial hypertension and increases in the respiratory rate, among others. Recurrent and frequent exposure to the outpouring of catecholamines associated with seizures in patients with pharamaco-resistant epilepsies may, for example, account for abnormalities that increase the risk of sudden death such as prolongation of the Q-T interval which leads (often fatal) tachyarrhythmias such as torsade de pointe. Further evidence in support of the role of catecholamines in SUDEP is found in autopsies of SUDEP victims, revealing interstitial myocardial fibrosis (a risk factor for lethal arrhythmias), myocyte vacuolization, atrophy of cardiomyocytes, leukocytic infiltration, and perivascular fibrosis. Restoration of the sympatho-parasympathetic tone to normal levels, a therapeutic objective that may be accomplished by enhancing para-sympathetic activity though among others, electrical stimulation of the vagus nerve, may decrease the rate and severity of cardiac and autonomic co-morbidities in these patients.

While there have been significant advances over the last several decades in treatments for epileptic seizures, the management of co-morbidities—in particular the cardiac alterations associated with seizures—remains largely unaddressed. There is a need for improved epilepsy treatments that address cardiac impairments associated with seizures. Pharmacological therapies for neurological diseases (including epilepsy) have been available for many decades. A more recent treatment for neurological disorders involves electrical stimulation of a target tissue to reduce symptoms or effects of the disorder. Such therapeutic electrical signals have been successfully applied to brain, spinal cord, and cranial nerves tissues improve or ameliorate a variety of conditions. A particular example of such a therapy involves applying an electrical signal to the vagus nerve to reduce or eliminate epileptic seizures, as described in U.S. Pat. Nos. 4,702,254, 4,867,164, and 5,025,807, which are hereby incorporated herein by reference in their entirety.

The endogenous electrical activity (i.e., activity attributable to the natural functioning of the patient's own body) of a neural structure may be modulated in a variety of ways. One such way is by applying exogenous (i.e., from a source other than the patient's own body) electrical, chemical, or mechanical signals to the neural structure. In some embodiments, the exogenous signal ("neurostimulation" or "neuromodulation") may involve the induction of afferent action potentials, efferent action potentials, or both, in the neural structure. In some embodiments, the exogenous (therapeutic) signal may block or interrupt the transmission of endogenous (natural) electrical activity in the target neural structure. Electrical signal therapy may be provided by implanting an electrical device underneath the skin of a patient and delivering an electrical signal to a nerve such as a cranial nerve.

In one embodiment, the electrical signal therapy may involve detecting a symptom or event associated with the patient's medical condition, and the electrical signal may be delivered in response to the detection. This type of stimulation is generally referred to as "closed-loop," "active," "feedback," "contingent" or "triggered" stimulation. Alternatively, the system may operate according to a predetermined program to periodically apply a series of electrical pulses to the nerve intermittently throughout the day, or over another predetermined time interval. This type of stimulation is generally referred to as "open-loop," "passive," "non-feedback," "non-contingent" or "prophylactic," stimulation.

In other embodiments, both open- and closed-loop stimulation modes may be used. For example, an open-loop electrical signal may operate as a "default" program that is repeated according to a programmed on-time and off-time until a condition is detected by one or more body sensors and/or algorithms. The open-loop electrical signal may then be interrupted in response to the detection, and the closed-loop electrical signal may be applied—either for a predetermined time or until the detected condition has been effectively treated. The closed-loop signal may then be interrupted, and the open-loop program may be resumed. Therapeutic electrical stimulation may be applied by an implantable medical device (IMD) within the patient's body or, in some embodiments, externally.

Closed-loop stimulation of the vagus nerve has been proposed to treat epileptic seizures. Many patients with intractable, refractory seizures experience changes in heart rate and/or other autonomic body signals near the clinical onset of seizures. In some instances the changes may occur prior to the clinical onset, and in other cases the changes may occur at or after the clinical onset. Where the changes involves heart rate, most often the rate increases, although in some instances a drop or a biphasic change (up-then-down or down-then-up) may occur. It is possible using a heart rate sensor to detect such changes and to initiate therapeutic electrical stimulation (e.g., VNS) based on the detected change. The closed-loop therapy may be a modified version of an open-loop therapy. See, e.g., U.S. Pat. Nos. 5,928,272, and 6,341,236, each hereby incorporated by reference herein. The detected change may also be used to warn a patient or third party of an impending or occurring seizure.

VNS therapy for epilepsy patients typically involves a train of electrical pulses applied to the nerve with an electrode pair including a cathode and an anode located on a left or right main vagal trunk in the neck (cervical) area. Only the cathode is capable of generating action potentials in nerve fibers within the vagus nerve; the anode may block some or all of the action potentials that reach it (whether endogenous or exogenously generated by the cathode). VNS as an epilepsy therapy involves modulation of one or more brain structures. Therefore, to prevent the anode from blocking action potentials generated by the cathode from reaching the brain, the cathode is usually located proximal to the brain relative to the anode. For vagal stimulation in the neck area, the cathode is thus usually the upper electrode and the anode is the lower electrode. This arrangement is believed to result in partial blockage of action potentials distal to or below the anode (i.e., those that would travel through the vagus nerve branches innervating the lungs, heart and other viscerae). Using an upper-cathode/lower-anode arrangement has also been favored to minimize any effect of the vagus nerve stimulation on the heart.

Stimulation of the left vagus nerve, for treatment of epilepsy has complex effects on heart rate (see Frei & Osorio, Epilepsia 2001), one of which includes slowing of the heart rate, while stimulation of the right vagus nerve has a more prominent bradycardic effect. Electrical stimulation of the right vagus nerve has been proposed for use in the operating room to slow the heart during heart bypass surgery, to provide a surgeon with a longer time period to place sutures between heartbeats (see, e.g., U.S. Pat. No. 5,651,373). Some patents discussing VNS therapy for epilepsy treatment express concern with the risk of inadvertently slowing the heart during stimulation. In U.S. Pat. No. 4,702,254, it is suggested that by locating the VNS stimulation electrodes below the inferior cardiac nerve, "minimal slowing of the heart rate is achieved" (col. 7 lines 3-5), and in U.S. Pat. No. 6,920,357, the use of a pacemaker to avoid inadvertent slowing of the heart is disclosed.

Cranial nerve stimulation has also been suggested for disorders outside the brain such as those affecting the gastrointestinal system, the pancreas (e.g., diabetes, which often features impaired production of insulin by the islets of Langerhans in the pancreas), or the kidneys. Electrical signal stimulation of either the brain alone or the organ alone may have some efficacy in treating such medical conditions, but may lack maximal efficacy.

While electrical stimulation has been used for many years to treat a number of conditions, a need exists for improved VNS methods of treating epilepsy and its cardiac co-morbidities as well as other brain and non-brain disorders.

SUMMARY OF THE INVENTION

In one aspect, the present invention relates to a method of treating a patient having epilepsy comprising coupling a first electrode and a second electrode to a vagus nerve of the patient, wherein the first electrode is coupled to a main trunk of a vagus nerve and the second electrode is coupled to a cardiac branch of a vagus nerve, providing an electrical signal generator coupled to the first electrode and the second electrode, receiving at least one body data stream, analyzing the at least one body data stream using a seizure or event detection algorithm to determine whether or not the patient has had an epileptic seizure, applying a first electrical signal from the electrical signal generator to the main trunk of a vagus nerve using the first electrode as a cathode, based on a determination that the patient has not had an epileptic seizure, and applying a second electrical signal from the electrical signal generator to the cardiac branch of the vagus nerve using the second electrode as a cathode, based on a determination that the patient has had an epileptic seizure.

In one aspect, the present invention relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing, in response to a determination that the patient has had an epileptic seizure, determining whether or not the seizure is characterized by an increase in the patient's heart rate, applying a first electrical signal to a main trunk of a vagus nerve of the patient using a first electrode as a cathode based on one of a) a determination that the patient has not had an epileptic seizure, and b) a determination that the patient has had an epileptic seizure that is not characterized by an increase in the patient's heart rate, wherein the first electrode is coupled to the main trunk, and applying a second electrical signal to a cardiac branch of a vagus nerve of the patient using a second electrode as a cathode based on a determination that the patient has had an epileptic seizure characterized by an increase in the patient's heart rate, wherein the second electrode is coupled to the cardiac branch.

In one aspect, the present invention relates to a system for treating a medical condition in a patient, comprising a first electrode and a second electrode coupled to a vagus nerve of the patient, wherein the first electrode is proximal to the brain relative to the second electrode, and the second electrode is coupled to a cardiac branch of the vagus nerve, a programmable electrical signal generator, a sensor for sensing at least one body data stream, a seizure detection module capable of analyzing the at least one body data stream and determining, based on the analyzing, whether or not the patient has had an epileptic seizure, and a logic unit for applying a first electrical signal to the vagus nerve using the first electrode as a cathode based upon a determination by the seizure detection module that the patient has not had an epileptic seizure, and for applying a second electrical signal to the vagus nerve using the second electrode as a cathode based upon a determination by the seizure detection module that the patient has had an epileptic seizure.

In one aspect, the present invention relates to a method of treating a patient having epilepsy comprising applying a first electrical signal to a main trunk of a vagus nerve of the patient, wherein the first electrical signal is an open-loop electrical signal having a programmed on-time and a programmed off-time, sensing at least one body signal of the patient, determining the start of an epileptic seizure based on the at least one body signal, determining whether or not the seizure is characterized by an increase in the patient's heart rate, applying a second, closed-loop electrical signal to the main trunk of the vagus nerve based on a determination that the epileptic seizure is not characterized by an increase in the patient heart rate, and applying a third, closed-loop electrical signal to a cardiac branch of a vagus nerve based on a determination that the seizure is characterized by an increase in the patient's heart rate, wherein the third electrical signal is applied to reduce the patient's heart rate.

In one aspect, the present invention relates to a method of treating a patient having epilepsy comprising sensing at least one body signal of the patient, determining whether or not the patient has had an epileptic seizure based on the at least one body signal, sensing a cardiac signal of the patient, in response to a determination that the patient has had an epileptic seizure, determining whether or not the seizure is characterized by an increase in the patient's heart rate, applying a first electrical signal to a left vagus nerve of the patient using a first electrode as a cathode based on one of a) a determination that the patient has not had an epileptic seizure, and b) a determination that the patient has had an epileptic seizure that is not characterized by an increase in the patient's heart rate, wherein the first electrode is coupled to the left vagus nerve, and applying a second electrical signal to a right vagus nerve of the patient using a second electrode as a cathode based on a determination that the patient has had an epileptic seizure characterized by an increase in the patient's heart rate, wherein the second electrode is coupled to the right vagus nerve.

In one aspect, the present invention relates to a method of treating a patient having epilepsy comprising sensing at least one body signal of the patient, determining whether or not the patient has had an epileptic seizure based on the at least one body signal, sensing a cardiac signal of the patient, in response to a determination that the patient has had an epileptic seizure, determining whether or not the seizure is associated with a change in the patient's cardiac signal, applying a first electrical signal to a left vagus nerve of the patient using a first electrode as a cathode based on one of a) a determination that the patient has not had an epileptic seizure, and b) a determination that the patient has had an epileptic seizure that is not associated with a change in the patient's cardiac signal, wherein the first electrode is coupled to the left vagus nerve, and applying a second electrical signal to a right vagus nerve of the patient using a second electrode as a cathode based on a determination that the patient has had an epileptic seizure associated with a change in the patient's cardiac signal, wherein the second electrode is coupled to the right vagus nerve.

In one aspect, the present invention relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing, in response to a determination that the patient has had an epileptic seizure, determining whether or not the seizure is characterized by cardiac changes, applying a first electrical signal to a left main trunk of a vagus nerve of the patient using a first electrode as a cathode based on one of a) a determination that the patient has not had an epileptic seizure, and b) a determination that the patient has had an epileptic seizure that is not characterized by cardiac changes, wherein the first electrode is coupled to the left main trunk, and applying a second electrical signal to a cardiac branch of a vagus nerve of the patient using a second electrode as a cathode based on a determination that the patient has had an epileptic seizure characterized by cardiac changes, wherein the second electrode is coupled to the cardiac branch.

BRIEF DESCRIPTION OF THE DRAWINGS

The invention may be understood by reference to the following description taken in conjunction with the accompanying drawings, in which like reference numerals identify like elements, and in which.

Figure 1A:
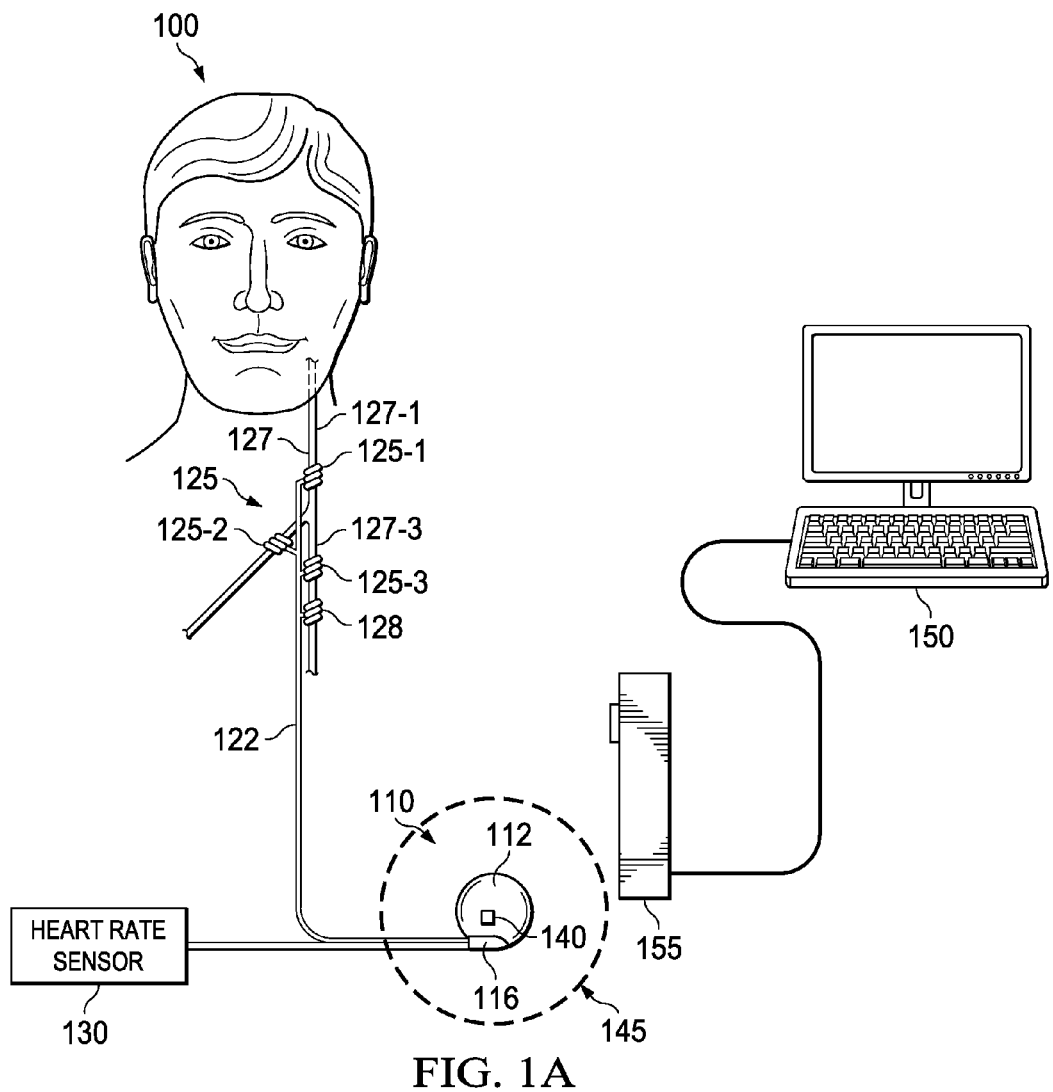
FIGS. 1A-1C provide stylized diagrams of an implantable medical device implanted into a patient's body for providing first and second electrical signals to a vagus nerve of a patient for treating epileptic seizures, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" is intended to mean either a direct or an indirect electrical connection. "Direct contact," "direct attachment," or providing a "direct coupling" indicates that a surface of a first element contacts the surface of a second element with no substantial attenuating medium there between. Small quantities of substances, such as bodily fluids, that do not substantially attenuate electrical connections do not vitiate direct contact. "Or" is used in the inclusive sense (i.e., "and/or") unless a specific use to the contrary is explicitly stated.

"Electrode" or "electrodes" may refer to one or more stimulation electrodes (i.e., electrodes for applying an electrical signal generated by an IMD to a tissue), sensing electrodes (i.e., electrodes for sensing a body signal), and/or electrodes capable of either stimulation or sensing. "Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to target neural tissue. A pulse may include both a therapeutic portion (in which most or all of the therapeutic or action-potential-generating effect occurs) and a charge-balancing portion in which the polarity of the electrodes are reversed and the electrical current is allowed to flow in the opposite direction to avoid electrode and/or tissue damage. Individual pulses are separated by a time period in which no charge is delivered to the nerve, which can be called the "interpulse interval." A "burst" is used herein to refer to a plurality of pulses, which may be separated from other bursts by an interburst interval in which no charge is delivered to the nerve. The interburst intervals have a duration exceeding the interpulse interval duration. In one embodiment, the interburst interval is at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

"Stimulate," "stimulating" and "stimulator" may generally refer to applying a signal, stimulus, or impulse to neural tissue (e.g., a volume of neural tissue in the brain or a nerve) for affecting it neuronal activity. While the effect of such stimulation on neuronal activity is termed "modulation," for simplicity, the terms "stimulating" and "modulating", and variants thereof, are sometimes used interchangeably herein. The modulation effect of a stimulation signal on neural tissue may be excitatory or inhibitory, and may potentiate acute and/or long-term changes in neuronal activity. For example, the modulation effect of a stimulation signal may comprise: (a) initiating action potentials in the target neural tissue; (b) inhibition of conduction of action potentials (whether endogenous or exogenously generated, or blocking their conduction (e.g., by hyperpolarizing or collision blocking), (c) changes in neurotransmitter/neuromodulator release or uptake, and (d) changes in neuro-plasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization.

A variety of stimulation therapies may be provided in embodiments of the present invention. Different nerve fiber types (e.g., A, B, and C-fibers that may be targeted) respond differently to stimulation from electrical signals because they have different conduction velocities and stimulation threshold. Certain pulses of an electrical stimulation signal, for example, may be below the stimulation threshold for a particular fiber and, therefore, may generate no action potential. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as a pre-pulse may be employed wherein axons of the target neural structure may be partially depolarized (e.g., with a pre-pulse or initial phase of a pulse) before a greater current is delivered to the target (e.g., with a second pulse or an initial phase such a stairstep pre-pulse to deliver a larger quantum of charge). Furthermore, opposing polarity phases separated by a zero current phase may be used to excite particular axons or postpone nerve fatigue during long term stimulation.

Cranial nerve stimulation, such as vagus nerve stimulation (VNS), has been proposed to treat a number of medical conditions, including epilepsy and other movement disorders, depression and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the variety of disorders for which cranial nerve stimulation has been proposed or suggested, the fact that detailed neural pathways for many (if not all) cranial nerves remain relatively unknown, makes predictions of efficacy for any given disorder difficult or impossible. Even if such pathways were known, the precise stimulation parameters that would modulate particular pathways relevant to a particular disorder generally cannot be predicted.

It appears that sympatho-vagal imbalance (lower vagal and higher sympathetic tone) plays an important role in generation of a wide spectrum of ictal and inter-ictal alterations in cardiac dynamics, ranging from rare uni-focal PVCs to cardiac death. Without being bound by theory, restoration of the vagal tone to a level sufficient to counteract the pathological effects of elevated catecholamines may serve a cardio-protective purpose that would be particularly beneficial in patients with pharmaco-resistant epilepsies, who are at highest risk for SUDEP.

In one embodiment, the present invention provides methods and apparatus to increase cardiac vagal tone in epilepsy patients by timely delivering therapeutic electrical currents to the trunks of the right or left vagus nerves or to their cardiac rami (branches), in response to increases in sympathetic tone, by monitoring among others, heart rate, heart rhythm, EKG morphology, blood pressure, skin resistance, catecholamine or their metabolites and neurological signals such as EEG/ECoG, kinetic (e.g., amplitude velocity, direction of movements) and cognitive (e.g., complex reaction time).

In one embodiment, the present invention provides a method of treating a medical condition selected from the group consisting of epilepsy, neuropsychiatric disorders (including but not limited to depression), eating disorders/obesity, traumatic brain injury, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

Figure 1B:
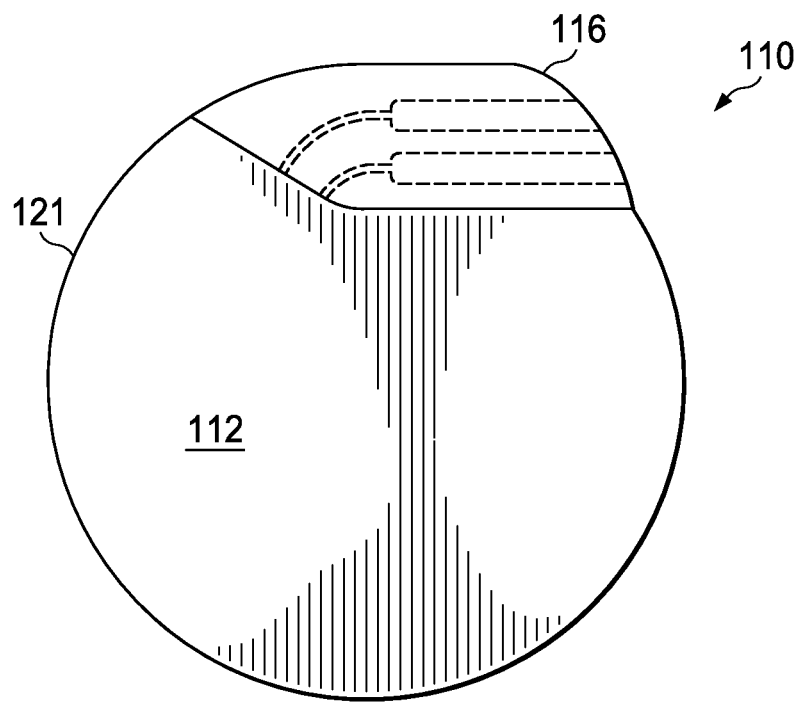
Figure 1C:
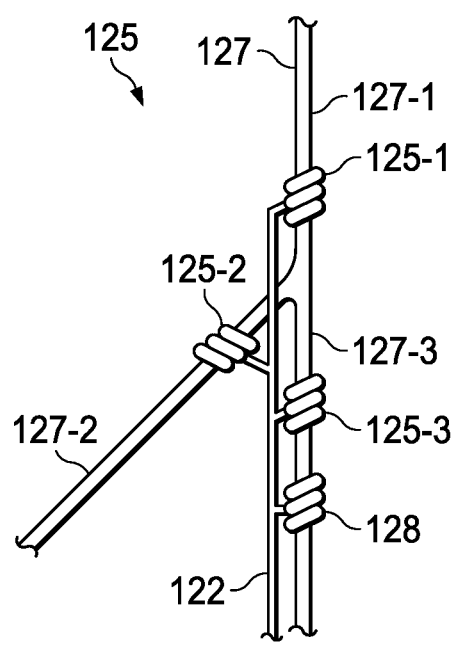

FIGS. 1A-1C depict a stylized implantable medical system 100 for implementing one or more embodiments of the present invention. FIGS. 1A-1C illustrate an electrical signal generator 110 having main body 112 comprising a case or shell 121 (FIG. 1B) with a header 116 (FIG. 1A, 1B) for connecting to a lead assembly 122. An electrode assembly 125 is provided at a distal end of lead assembly 122, and includes one or more electrodes 125-1, 125-2, 125-3 that may be coupled to a neural target tissue such as a vagus nerve 127, which may include an upper main trunk portion 127-1 above a cardiac branch and a lower main trunk portion 127-3 below a cardiac branch.

Electrode assembly 125, preferably comprising at least an electrode pair, is conductively connected to the distal end of an insulated, electrically conductive lead assembly 122, which preferably comprises a pair of lead wires (one wire for each electrode of an electrode pair). Lead assembly 122 is attached at its proximal end to one or more connectors on header 116 (FIG. 1B) on case 121. Electrode assembly 125 may be surgically coupled to a cranial nerve, such as vagus nerve 127 in the patient's neck or another location, e.g., near the diaphragm. In alternative embodiments, the therapeutic electrical signal may also be applied to other cranial nerves, such as the trigeminal nerve.

In one embodiment, at least one electrode 125-1 may be coupled to an upper main trunk 127-1 of the vagus nerve, and at least one electrode 125-2 may be coupled to a cardiac branch 127-2 of the vagus nerve. Main trunk electrode 125-1 may be used to provide a first electrical signal to the main trunk 127-1, and cardiac branch electrode 125-2 may be used to provide a second electrical signal to cardiac branch 127-2. The first electrical signal may generate afferent action potentials to modulate electrical activity of the patient's brain without significantly affecting the patient's heart rate. The second electrical signal may generate efferent action potentials to module the cardiac activity of the patient, and in particular may slow the patient's heart rate and maintain or restore a sympathetic/parasympathetic balance to physiological levels. In an alternative embodiment, an electrode 125-3 may be coupled to a lower main trunk 127-3 of the vagus nerve, either in addition to or instead of the upper main trunk electrode 125-1. Suitable electrode assemblies are available from Cyberonics, Inc., Houston, Tex., USA as the Model 302, PerenniaFlex and PerenniaDura electrode assemblies. Persons of skill in the art will appreciate, however, that many electrode designs could be used in embodiments of the present invention, including unipolar electrodes.

In some embodiments, a heart rate sensor 130, and/or a kinetic sensor 140 (e.g., a triaxial accelerometer) may be included in the system 100 to sense one or more of a cardiac signal or data stream and a kinetic data stream of the patient. In one embodiment, the heart rate sensor may comprise a separate element 130 that may be coupled to generator 110 through header 116 as illustrated in FIG. 1A. In another embodiment, the electrodes 125-1, 125-2, 125-3 and/or the case 121 may be used as sensing electrodes to sense heart rate. An accelerometer may be provided inside generator 110 in one embodiment to sense a kinetic signal (e.g., body movement) of the patient. One or more of the heart rate sensor 130 and the kinetic sensor 140 may be used by a seizure detection algorithm in the system 100 to detect epileptic seizures. In alternative embodiments, other body signals (e.g., blood pressure, brain activity, blood oxygen/CO2 concentrations, temperature, skin resistivity, etc.) of the patient may be sensed and used by the seizure detection algorithm to detect epileptic seizures. Signal generator 110 may be implanted in the patient's chest in a pocket or cavity formed by the implanting surgeon below the skin (indicated by line 145, FIG. 1A).

Returning to FIGS. 1A and 1C, a first electrode 125-1 may be wrapped or otherwise electrically coupled to an upper main trunk 127-1 of a vagus nerve 127 of the patient, and a second electrode 125-2 may be wrapped or coupled to a cardiac branch 127-2 of the vagus nerve. In one embodiment, a third electrode 125-3 may be coupled to a lower main trunk 127-3 of the vagus nerve below the cardiac branch 127-2 of the vagus nerve, instead of or in addition to first electrode 125-1 coupled to the upper main trunk above the cardiac branch. In some embodiments, third electrode 125-3 may be omitted. Electrode assembly 125 may be secured to the nerve by a spiral anchoring tether 128 (FIG. 1C), which does not include an electrode. Lead assembly 122 may further be secured, while retaining the ability to flex, by a suture connection 130 to nearby tissue (FIG. 1C).

In one embodiment, the open helical design of the electrodes 125-1, 125-2, 125-3 is self-sizing, flexible, minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises an electrode ribbon (not shown) for each of electrodes 125-1, 125-2, 125-3, made of a conductive material such as platinum, iridium, platinum-iridium alloys, and/or oxides thereof. The electrode ribbons are individually bonded to an inside surface of an elastomeric body portion of the spiral electrodes 125-1, 125-2, 125-3 (FIG. 1C), which may comprise spiral loops of a multi-loop helical assembly. Lead assembly 122 may comprise three distinct lead wires or a triaxial cable that are respectively coupled to one of the conductive electrode ribbons. One suitable method of coupling the lead wires to the electrodes 125-1, 125-2, 125-3 comprises a spacer assembly such as that disclosed in U.S. Pat. No. 5,531,778, although other known coupling methods may be used.

The elastomeric body portion of each loop may be composed of silicone rubber or other biocompatible elastomeric compounds, and the fourth loop 128 (which may have no electrode in some embodiments) acts as the anchoring tether for the electrode assembly 125.

In one embodiment, electrical pulse generator 110 may be programmed with an external computer 150 using programming software known in the art for stimulating neural structures, and a programming wand 155 to facilitate radio frequency (RF) communication between the external computer 150 (FIG. 1A) and the implanted pulse generator 110. In one embodiment, wand 155 and software permit wireless, non-invasive communication with the generator 110 after implant. Wand 155 may be powered by internal batteries, and provided with a "power on" light to indicate sufficient power for communications. Another indicator light may be provided to show that data transmission is occurring between the wand and the generator. In other embodiments, wand 155 may be omitted, e.g., where communications occur in the 401-406 MHz bandwidth for Medical Implant Communication Service (MICS band).

In some embodiments of the invention, a body data stream may be analyzed to determine whether or not a seizure has occurred. Many different body data streams and seizure detection indices have been proposed for detecting epileptic seizures. Additional details on method of detecting seizure from body data are provided in co-pending U.S. patent application Ser. No. 12/896,525, filed Oct. 1, 2010, 13/098,262, filed Apr. 29, 2011, and 13/288,886, filed Nov. 3, 2011, each hereby incorporated by reference in its entirety herein. Seizure detection based on the patient's heart rate (as sensed by implanted or external electrodes), movement (as sensed by, e.g., a triaxial accelerometer), responsiveness, breathing, blood oxygen saturation, skin resistivity/conductivity, temperature, brain activity, and a number of other body data streams are provided in the foregoing co-pending applications.

In one embodiment, the present invention provides a method for treating a patient with epilepsy in which a body data stream is analyzed using a seizure detection algorithm to determine whether or not the patient has had an epileptic seizure. If the analysis results in a determination that the patient has not had an epileptic seizure, a signal generator may apply a first electrical signal to a main trunk of a vagus nerve of the patient. If the analysis results in a determination that the patient has had an epileptic seizure, the signal generator may apply a second electrical signal to a cardiac branch of a vagus nerve of the patient. In some embodiments, the application of the first electrical signal to the main trunk is terminated, and only the second electrical signal to the cardiac branch is provided once a seizure is detected.

In alternative embodiments, both the first and second electrical signals may be applied to the main trunk and cardiac branch, respectively, of the vagus nerve in response to a determination that the patient has had a seizure (i.e., the first electrical signal continues to be applied to the main trunk of the vagus nerve and the second signal is initiated). Where both the first and second electrical signals are provided, the two signals may be provided sequentially, or in alternating fashion to the main trunk and the cardiac branch by controlling the polarity of the electrodes on the main trunk and cardiac branch. In one embodiment, the first signal may be provided to the main trunk by using one of the upper main trunk electrode 125-1 or the lower main trunk electrode 125-3 as the cathode and the cardiac branch electrode 125-2 as the anode, or by using both of the upper main trunk electrode and the lower main trunk electrode as the cathode and the anode. The second signal may be provided (e.g., by rapidly changing the polarity of the electrodes) by using the cardiac branch electrode 125-2 as the cathode and a main trunk electrode 125-1 or 125-3 as the anode.

In still other embodiments, the second electrical signal is applied to the cardiac branch of the vagus nerve only of the analysis results in a determination that the patient has had an epileptic event that is accompanied by an increase in heart rate, and the second electrical signal is used to lower the heart rate back towards a rate that existed prior to the seizure onset. Without being bound by theory, the present inventors believe that slowing the heart rate at the onset of seizures—particularly where the seizure is accompanied by an increase in heart rate—may improve the ability of VNS therapy to provide cardio-protective benefits.

Prior patents describing vagus nerve stimulation as a medical therapy have cautioned that undesired slowing of the heart rate may occur, and have proposed various methods of avoiding such a slowing of the heart rate. In U.S. Pat. No. 6,341,236, it is suggested to sense heart rate during delivery of VNS and if a slowing of the heart rate is detected, either suspending delivery of the VNS signal or pacing the heart using a pacemaker. The present application discloses a VNS system that detects epileptic seizures, particularly epileptic seizures accompanied by an increase in heart rate, and intentionally applies an electrical signal to slow the heart rate in response to such a detection. In another aspect, the present application discloses VNS systems that provide a first electrical signal to modulate only the brain during periods in which no seizure has been detected, and either 1) a second electrical signal to modulate only the heart (to slow its rate) or 2) both a first electrical signal to the brain and a second electrical signal to the heart, in response to a detection of the onset of an epileptic seizure. These electrical signals may be delivered simultaneously, sequentially (e.g., delivery of stimulation to the brain precedes delivery of stimulation to the heart or vice versa), or delivery may be interspersed/interleaved.

The first electrode may be used as a cathode to provide an afferent first electrical signal to modulate the brain of the patient via main trunk electrode 125-1. Either second electrode 125-2 or a third electrode 125-3 may be used as an anode to complete the circuit. The second electrode may be used as a cathode to provide an efferent second electrical signal to slow the heart rate of the patient via cardiac branch electrode 125-2. Either first electrode 125-1 or a third electrode 125-3 may be used as an anode to complete the circuit. In one embodiment, the first electrical signal may be applied to the upper (127-1) or lower (127-3) main trunk of the vagus nerve in an open-loop manner according to programmed parameters including an off-time and an on-time. The on-time and off-time together establish the duty cycle determining the fraction of time that the signal generator applies the first electrical. In one embodiment, the off-time may range from 7 seconds to several hours or even longer, and the on-time may range from 5 seconds to 300 seconds. It should be noted that the duty cycle does not indicate when current is flowing through the circuit, which is determined from the on-time together with the pulse frequency (usually 10-200, Hz, and more commonly 20-30 Hz) and pulse width (typically 0.1-0.5 milliseconds). The first electrical signal may also be defined by a current magnitude (e.g., 0.25-3.5 milliamps), and possibly other parameters (e.g., pulse width, and whether or not a current ramp-up and/or ramp-down is provided, a frequency, and a pulse width.

In one embodiment, a seizure detection may result in both applying the first electrical signal to provide stimulation to the brain in close proximity to a seizure detection (which may interrupt or terminate the seizure), as well as application of the second electrical signal which may slow the heart, thus exerting a cardio-protective effect. In a particular embodiment, the second electrical signal is applied only in response to a seizure detection that is characterized by (or accompanied or associated with) an increase in heart rate, and is not applied in response to seizure detections that are not characterized by an increase in heart rate. In this manner, the second electrical signal may help interrupt the seizure by restoring the heart to a pre-seizure baseline heart rate when the patient experiences ictal tachycardia (elevated heart rate during the seizure), while leaving the heart rate unchanged if the seizure has no significant effect on heart rate.

In still further embodiments, additional logical conditions may be established to control when the second electrical signal is applied to lower the patient's heart rate following a seizure detection. In one embodiment, the second electrical signal is applied only if the magnitude of the ictal tachycardia rises above a defined level. In one embodiment, the second electrical signal is applied to the cardiac branch only if the heart rate increases by a threshold amount above the pre-ictal baseline heart rate (e.g., more than 20 beats per minute above the baseline rate). In another embodiment, the second electrical signal is applied to the cardiac branch only if the heart rate exceeds an absolute heart rate threshold (e.g., 100 beats per minute, 120 beats per minute, or other programmable threshold). In a further embodiment, a duration constraint may be added to one or both of the heart rate increase or absolute heart rate thresholds, such as a requirement that the heart rate exceed the baseline rate by 20 beats per minute for more than 10 seconds, or exceed 110 beats per minute for more than 10 seconds, before the second electrical signal is applied to the cardiac branch in response to a seizure detection.

In another embodiment, the heart rate sensor continues to monitor the patient's heart rate during and/or after application of the second electrical signal, and the second electrical signal is interrupted or terminated if the patient's heart rate is reduced below a low heart rate threshold, which may be the baseline heart rate that the patient experienced prior to the seizure, or a rate lower or higher than the baseline pre-ictal heart rate. The low rate threshold may provide a measure of safety to avoid undesired events such as bradycardia and/or syncope.

In yet another embodiment, heart rate sensor 130 may continue to monitor heart rate and/or kinetic sensor 140 may continue to monitor body movement in response to applying the second electrical signal, and the second electrical signal may be modified (e.g., by changing one or more parameters such as pulse frequency, or by interrupting and re-initiating the application of the second electrical signal to the cardiac branch of the vagus nerve) to control the heart rate below an upper heart rate threshold and/or body movement exceeds one or more movement thresholds. For example, the frequency or duration of the second electrical signal applied to the cardiac branch of the vagus nerve may be continuously modified based the instantaneous heart rate as monitored during the course of a seizure to control what would otherwise be an episode of ictal tachycardia below an upper heart rate threshold. In one exemplary embodiment, the second electrical signal may be programmed to provide a 30-second pulse burst at 30 Hz, with the pulses having a pulse width of 0.25 milliseconds and a current of 1.5 milliamps. If, at the end of the 30 second burst, the heart rate remains above 120 beats per minute, and is continuing to rise, the burst may be extended to 1 minute instead of 30 seconds, the frequency may be increased to 50 Hz, the pulse width may be increased to 350 milliseconds, or combinations of the foregoing. In still further embodiments, additional therapies (e.g., oxygen delivery, drug delivery, cooling therapies, etc.) may be provided to the patient if the body data (heart rate, kinetic activity, etc.) indicates that the patient's seizure is not under control or terminated.

Abnormalities in EKG morphology or rhythm may also trigger delivery of current to the heart via the trunks of vagi or its cardiac rami. In other embodiments, pharmacological agents such as beta-blockers may be automatically released into a patient's blood stream in response to the detection of abnormal heart activity during or between seizures.

In one embodiment, the first electrical signal and the second electrical signal are substantially identical. In another embodiment, the first electrical signal may vary from the second electrical signal in terms of one or more of pulse width, number of pulses, amplitude, frequency, stimulation on-time, and stimulation off-time, among other parameters.

The number of pulses applied to the main trunk or cardiac branch, respectively, before changing the polarity of the first and second electrodes need not be one. Thus, two or more pulses may be applied to the main trunk before applying pulses to the cardiac branch of the vagus nerve. More generally, the first and second signals can be independent of one another and applied according to timing and programming parameters controlled by the controller 210 and stimulation unit 220.

In one embodiment, one or more pulse bursts of the first electrical signal are applied to the main trunk of the vagus nerve in response to a detected seizure before applying one or more bursts of the second electrical signal to the cardiac branch. In another embodiment, the first and second signals are interleaved on a pulse-by-pulse basis under the control of the controller 210 and stimulation unit 220.

Typically, VNS can be performed with pulse frequency of 20-30 Hz (resulting in a number of pulses per burst of 140-1800, at a burst duration from 7-60 sec). In one embodiment, at least one of the first electrical signal and the second electrical signal comprises a microburst signal. Microburst neurostimulation is discussed by U.S. Ser. No. 11/693,451, filed Mar. 2, 2007 and published as United States patent Publication No. 20070233193, and incorporated herein by reference in its entirety. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

Cranial nerves such as the vagus nerve include different types of nerve fibers, such as A-fibers, B-fibers and C-fibers. The different fiber types propagate action potentials at different velocities. Each nerve fiber can propagate action potentials in only one direction (e.g., afferently to the brain or efferently to the heart and/or viscera). Moreover, only the cathode can generate action potentials (by depolarizing axons). It is believed that the anode may block at least some action potentials traveling to it from the cathode. For example, referring to FIG. 1, both afferent and efferent action potentials may be generated in an upper main trunk of vagus nerve 127-1 by applying a pulse to the nerve using upper main trunk electrode 125-1 as a cathode and cardiac branch electrode 125-2 as an anode. Efferent action potentials generated at upper main trunk electrode 125-1 and traveling toward the heart on cardiac branch 127-2 may be blocked by cardiac branch anode 125-2. Efferent action potentials traveling from the upper main trunk 127-1 to the lower organs in lower main trunk 127-3 may be either blocked (by using lower main trunk electrode 125-3 as an anode either with or instead of cardiac branch electrode 125-2) or allowed to travel to the lower organs (by not using electrode structure 125-3 as an electrode).

Efferent action potentials may be generated and allowed to travel to the heart by reversing the polarity of the electrodes and applying a second electrical signal to the upper main trunk electrode 125-1 and cardiac branch electrode 125-2. If cardiac branch electrode 125-2 is used as a cathode, action potentials traveling efferently to the heart in cardiac branch 127-2 will not be blocked in the embodiment of FIG. 1, while at least some afferent action potentials generated traveling toward the brain may be blocked by upper electrode 125-2, which functions as the anode for the second electrical signal.

In a further embodiment of the invention, rapid changes in electrode polarity may be used to generate action potentials to collision block action potentials propagating in the opposite direction. To generalize, in some embodiments, the vagus nerve can be selectively stimulated to propagate action potentials either afferently (i.e., to the brain) or efferently (i.e., to the heart and/or lower organs/viscerae).

Figure 2:
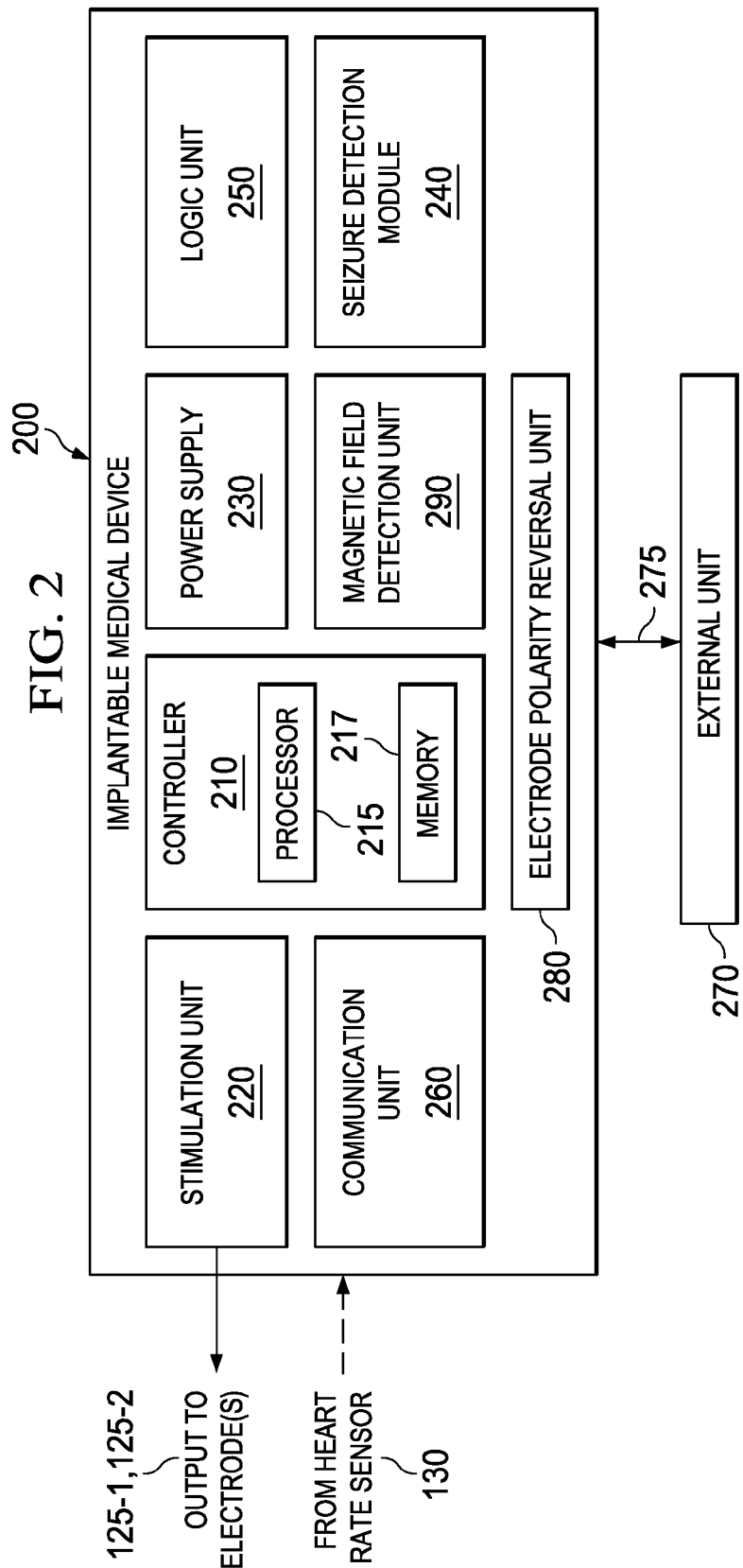
FIG. 2 illustrates a block diagram depiction of an implantable medical device of FIG. 1, in accordance with one illustrative embodiment of the present invention.

Turning now to FIG. 2, a block diagram depiction of an implantable medical device, in accordance with one illustrative embodiment of the present invention is illustrated. The IMD 200 may be coupled to various electrodes 125 via lead(s) 122 (FIGS. 1A, 1C). First and second electrical signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2, 125-3 (FIG. 1A).

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, may perform stimulation based on internal calculations and programming, and may receive and/or process sensor data received from one or more body data sensors such as electrodes 125-1, 125-2, 125-3, or heart rate sensor 130. The controller 210 is capable of affecting substantially all functions of the IMD 200.

The controller 210 may comprise various components, such as a processor 215, a memory 217, etc. The processor 215 may comprise one or more micro controllers, micro processors, etc., that are capable of executing a variety of software components. The processor may receive, pre-condition and/or condition sensor signals, and may control operations of other components of the IMD 200, such as stimulation unit 220, seizure detection module 240, logic unit 250, communication unit, 260, and electrode polarity reversal unit 280. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, first electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

Signals from sensors (electrodes that are used to sense one or more body parameters such as temperature, heart rate, brain activity, etc.) may be provided to the IMD 200. The body signal data from the sensors may be used by a seizure detection algorithm embedded or processed in seizure detection unit 250 to determine whether or not the patient has had an epileptic seizure. The seizure detection algorithm may comprise hardware, software, firmware or combinations thereof, and may operate under the control of the controller 210. Although not shown, additional signal conditioning and filter elements (e.g., amplifiers, D/A converters, etc., may be used to appropriately condition the signal for use by the seizure detection unit 250. Sensors such as heart sensor 130 and kinetic sensor 140 may be used to detect seizures, along with other autonomic, neurologic, or other body data.

The IMD 200 may also comprise an electrode polarity reversal unit 280. The electrode polarity reversal unit 280 is capable of reversing the polarity of electrodes (125-1, 125-2, 125-3) associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data and/or seizure detection data to the patient, a physician, or another party.

In one embodiment, a method of treating an epileptic seizure is provided that involves providing simultaneously both a first electrical signal to a main trunk of a vagus nerve and a second electrical signal to a cardiac branch of the vagus nerve. The method may be achieved using only two electrodes by providing a polarity reversal unit to rapidly reverse the polarity of the first and second electrodes. The method includes sensing a cardiac signal and a kinetic signal of the patient, and detecting a seizure event with a seizure detection algorithm. The timing of pulses for the first and second electrical signals may be determined by controller 210 in conjunction with stimulation unit 220. When beneficial, steps to avoid collisions of actions potentials travelling in opposite directions may be implemented, while steps to promote collisions may be taken when clinically indicated.

To provide simultaneous first and second electrical signals to the main trunk and cardiac branch, a pulse of the first electrical signal is generated with the electrical signal generator 110 and applied to the main trunk of the vagus nerve using the first electrode 125-1 as a cathode and the second electrode as an anode. The polarity of the electrodes is then reversed by the polarity reversal unit 280, yielding a configuration wherein the first electrode is an anode and the second electrode is a cathode. A pulse of the second electrical signal (having the appropriate pulse width and current) is generated and applied (under appropriate timing control by controller 110 and stimulation unit 220) to the cardiac branch of the vagus nerve using the second electrode 125-2 as a cathode and first electrode 125-1 as an anode. The polarities of the electrodes may then be reversed by polarity reversal unit 280 under the control of controller 210, and another pulse of the first electrical signal may be generated and applied to the main trunk under timing and parameter control of controller 210 and stimulation unit 220. By rapidly (within a few microseconds) switching the polarities of the electrodes 125-1 and 125-2, the first and second electrical signals may be interleaved and provided simultaneously to the main trunk and cardiac branches of the vagus nerve.

The IMD 200 is capable of delivering stimulation that can be contingent, periodic, random, coded, and/or patterned. The stimulation signals may comprise an electrical stimulation frequency of approximately 0.1 to 2500 Hz. The stimulation signals may comprise a pulse width in the range of approximately 1-2000 micro-seconds. The stimulation signals may comprise current amplitude in the range of approximately 0.1 mA to 10 mA. Appropriate precautions may be taken to avoid delivering injurious current densities to target neural tissues, e.g., by selecting current, voltage, frequency, pulse width, on-time and off-time parameters to maintain current density below thresholds for damaging tissues.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an input to implement a particular first or second electrical signal (or both) for application to the main trunk of cardiac branches, respectively, of the vagus nerve.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
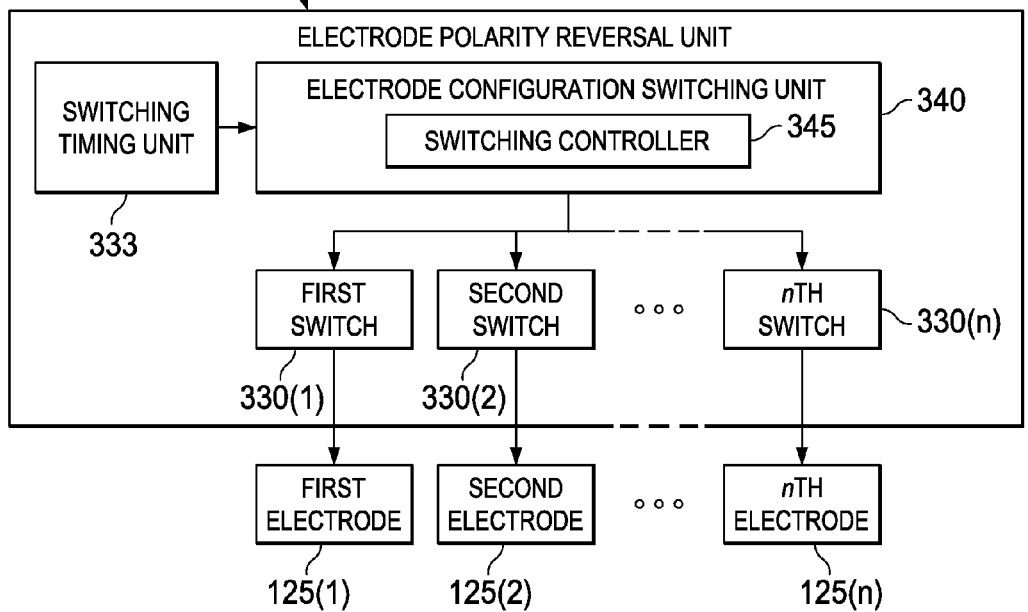
FIG. 3 illustrates a block diagram depiction of an electrode polarity reversal unit shown in FIG. 2, in accordance with one illustrative embodiment of the present invention.

FIG. 3 shows in greater detail an electrode polarity reversal unit 280 (FIG. 2) in one embodiment. The electrode polarity reversal unit 280 comprises an electrode configuration switching unit 340, which includes a switching controller 345. The switching controller 345 transmits signals to one or more switches, generically, n switches 330(1), 330(2), . . . 330(n) which effect the switching of the configuration of two or more electrodes, generically, n electrodes 125(1), 125(2), . . . 125(n). Although FIG. 3 shows equal numbers of switches 330 and electrodes 125, persons of skill in the art having the benefit of the present disclosure will understand that the number of switches 330 and their connections with the various electrodes 125 can be varied as a matter of routine optimization. A switching timing unit 333 can signal to the electrode configuration switching unit 340 that a desired time for switching the electrode configuration has been reached.

Instructions for implementing two or more stimulation regimens, which may include at least one open-loop electrical signal and at least one closed-loop electrical signal, may be stored in the IMD 200. These stimulation signals may include data relating to the type of stimulation signal to be implemented. In one embodiment, an open-loop signal may be applied to generate action potentials for modulating the brain of the patient, and a closed-loop signal may be applied to generate either action potentials for slowing the heart rate of the patient, or both action potentials to modulate the brain of the patient as well as action potentials for slowing the heart rate of the patient. In some embodiments, the open-loop and closed-loop signals may be provided to different target portions of a vagus nerve of the patient by switching the polarity of two or more electrodes using an electrode polarity reversal unit as described in FIG. 3 above. In alternative embodiments, additional electrodes may be provided to generate each of the open-loop and closed-loop signals without electrode switching.

In one embodiment, a first open-loop mode of stimulation may be used to provide an electrical signal to a vagus nerve using a first electrode as a cathode on a main trunk (e.g., 127-1 or 127-3 using electrodes 125-1 or 125-3, respectively) of a vagus nerve, and a second electrode as an anode on either a main trunk (e.g., electrode 125-3, when electrode 125-1 is used as a cathode) or cardiac branch (e.g., electrode 125-2) of a vagus nerve. The first open-loop signal may include a programmed on-time and off-time during which electrical pulses are applied (the on-time) and not-applied (the off-time) in a repeating sequence to the vagus nerve.

A second, closed-loop signal may be provided in response to a detected event (such as an epileptic seizure, particularly when accompanied by an increase in the patient's heart rate) using a different electrode configuration than the first, open-loop signal. In one embodiment, the second, closed-loop signal is applied to a cardiac branch using the second electrode 125-2 as a cathode and the first electrode on the main trunk (e.g., 125-1 or 125-3) as an anode. The second, closed-loop signal may involve generating efferent action potentials on the cardiac branch of the vagus nerve to slow the heart rate. In some embodiments, the first, open-loop signal may be interrupted/suspended in response to the detected event, and only the second, closed-loop signal is applied to the nerve. In other embodiments, the first, open loop signal may not be interrupted when the event is detected, and both the first, open-loop signal and the second, closed-loop signal are applied to the vagus nerve. In another embodiment, a third, closed-loop signal may also be provided in response to the detected event. The third, closed-loop signal may involve an electrical signal using the same electrode configuration as the first, open-loop electrical signal, but may provide a different electrical signal to the main trunk of the vagus nerve than either the first, open-loop signal or the second, closed-loop signal. The first, open-loop signal may be interrupted, terminated or suspended in response to the detected event, and the third, closed-loop signal may be applied to the nerve either alone or with the second, closed-loop signal. In some embodiments, both the second and third closed-loop signals may be provided in response to a detected epileptic seizure by rapidly changing the polarity of the first (125-1) and second (125-2) electrodes from cathode to anode and back, as pulses are provided as part of the second and third electrical signals, respectively. In one embodiment, the third electrical signal may involve modulating the brain by using a main trunk electrode (e.g., upper main trunk electrode 125-1) as a cathode and another electrode (e.g., cardiac branch electrode 125-2 or lower main trunk electrode 125-3) as an anode. The third electrical signal may comprise, for example, a signal that is similar to the first electrical signal but which provides a higher electrical current than the first electrical signal, and for a longer duration than the first signal or for a duration that is adaptively determined based upon a sensed body signal (in contrast, for example, to a fixed duration of the first electrical signal determined by a programmed on-time). By rapidly changing polarity of the electrodes, pulses for each of the second and third electrical signals may be provided such that the second and third signals are provided simultaneously to the cardiac branch and main trunk of the vagus nerve. In other embodiments, the first, second and third electrical signals may be provided sequentially rather than simultaneously.

In some embodiments, one or more of the first, second and third electrical signals may comprise a microburst signal, as described more fully in U.S. patent application Ser. Nos. 11/693,421, 11/693,451, and 11/693,499, each filed Mar. 29, 2007 and each hereby incorporated by reference herein in their entirety.

In one embodiment, each of a plurality of stimulation regimens may respectively relate to a particular disorder, or to particular events characterizing the disorder. For example, different electrical signals may be provided to one or both of the main trunk and cardiac branches of the vagus nerve depending upon what effects accompany the seizure. In a particular embodiment, a first open-loop signal may be provided to the patient in the absence of a seizure detection, while a second, closed-loop signal may be provided when a seizure is detected based on a first type of body movement of the patient as detected by, e.g., an accelerometer, a third, closed-loop signal may be provided when the seizure is characterized by a second type of body movement, a fourth, closed-loop signal may be provided when the seizure is characterized by an increase in heart rate, a fifth, closed-loop signal may be provided when the seizure is characterized by a decrease in heart rate, and so on. More generally, stimulation of particular branches or main trunk targets of a vagus nerve may be provided based upon different body signals of the patient. In some embodiments, additional therapies may be provided based on different events that accompany the seizure, e.g., stimulation of a trigeminal nerve or providing a drug therapy to the patient through a drug pump. In one embodiment, different regimens relating to the same disorder may be implemented to accommodate improvements or regressions in the patient's present condition relative to his or her condition at previous times. By providing flexibility in electrode configurations nearly instantaneously, the present invention greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches 330(1-n) may be electrical devices, electro-mechanical devices, and/or solid state devices (e.g., transistors).

Figure 4:
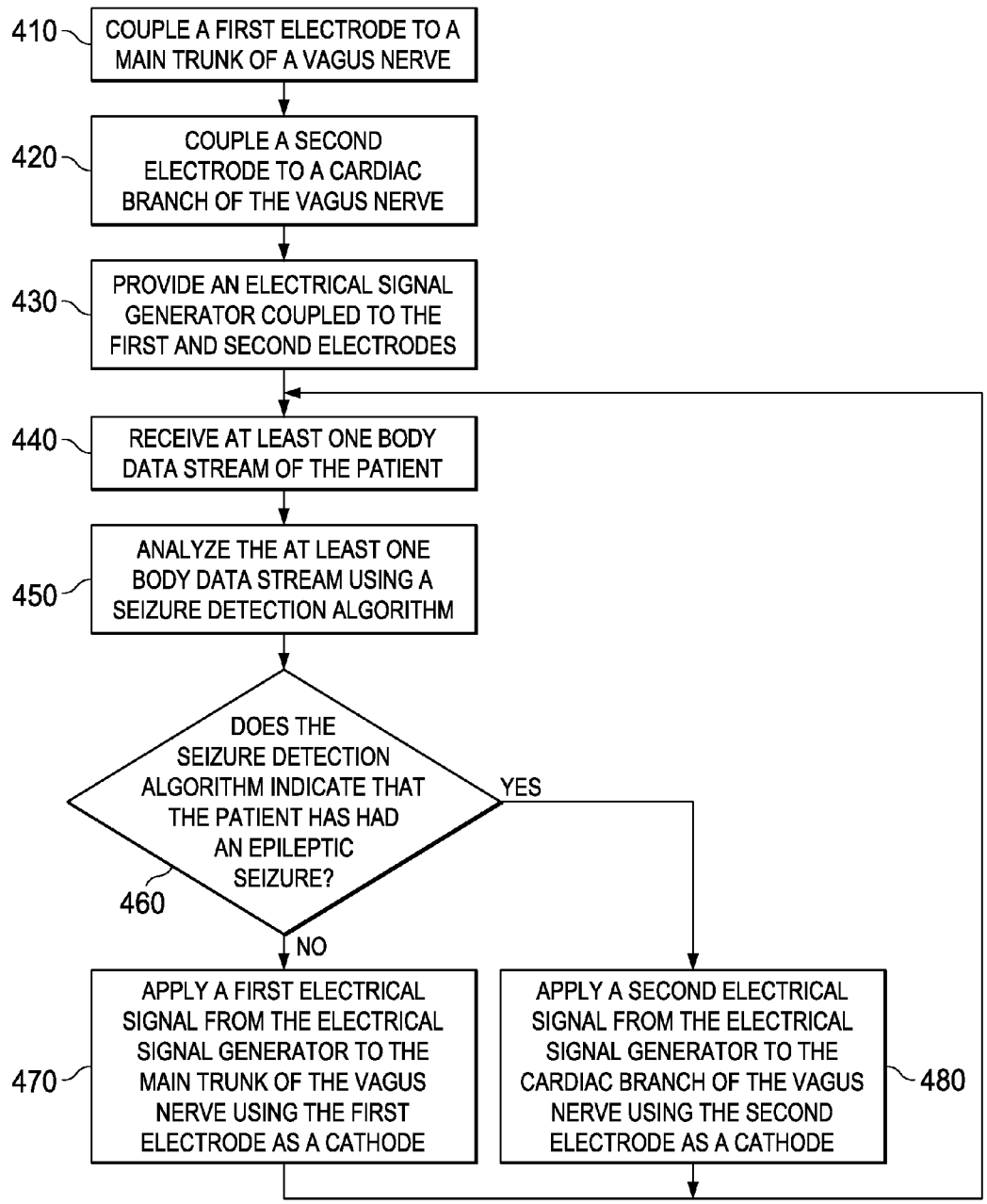
FIG. 4 illustrates a flowchart depiction of a method for providing first and second electrical signals to a main trunk and a cardiac branch of a vagus nerve, respectively, based upon whether or not the patient has had an epileptic seizure, in accordance with an illustrative embodiment of the present invention.

FIG. 4 shows one embodiment of a method of treating a patient having epilepsy according to the present invention. In this embodiment, a first electrode is coupled to a main trunk of a vagus nerve of the patient (410) and a second electrode is coupled to a cardiac branch of the vagus nerve (420). An electrical signal generator is coupled to the first and second electrodes (430).

The method further involves receiving at least one body data stream of the patient (440). The data may be sensed by a sensor such as heart rate sensor 130 (FIG. 1A) or a sensor that is an integral part of, or coupled to, an IMD 200 (FIG. 2) such as electrical pulse generator 110 (FIG. 1A), and the IMD may also receive the data from the sensor. The at least one body data stream is then analyzed using a seizure detection algorithm (450), and the seizure detection algorithm determines whether or not the patient has had an epileptic seizure (460).

If the algorithm indicates that the patient has not had an epileptic seizure, the method comprises applying a first electrical signal from the electrical signal generator to the main trunk of a vagus nerve using the first electrode as a cathode (470). In one embodiment, applying the first electrical signal comprises continuing to apply a programmed, open-loop electrical signal periodically to the main trunk of the vagus nerve according a programmed on-time and off-time.

If the algorithm indicates that the patient has had an epileptic seizure, the method comprises applying a second electrical signal from the electrical signal generator to the cardiac branch of the vagus nerve using the second electrode as a cathode (480). Depending upon which electrical signal (first or second) is applied, the method may involve changing the polarity of one or both of the first electrode and the second electrode. In one embodiment, the method may comprise suspending the first electrical and applying the second electrical signal. In one embodiment, the method comprises continuing to receive at least one body data stream of the patient at 440 after determining whether or not the patient has had an epileptic seizure.

In an alternative embodiment, if the seizure detection algorithm indicates that the patient has had an epileptic seizure, both the first electrical signal and the second electrical signal are applied to the main trunk and cardiac branches of a vagus nerve of the patient, respectively, at step 480. In a specific implementation of the alternative embodiment, pulses of the first and second electrical signal are applied to the main trunk and cardiac branch of the vagus nerve under the control of controller 210 by rapidly changing the polarity of the first and second electrodes using the electrode polarity reversal unit 280 to apply the first electrical signal to the main trunk using the first electrode as a cathode and the second electrode as an anode, changing the polarity of the first and second electrodes, and applying the second electrical signal to the cardiac branch using the second electrode as a cathode and the first electrode as an anode. Additional pulses for each signal may be similarly applied by rapidly changing the polarity of the electrodes.

In some embodiments, the first electrical signal and the second electrical signal are applied unilaterally, i.e., to a vagal main trunk and a cardiac branch on the same side of the body.

In other embodiments, the first and second electrical signals are applied bilaterally, i.e., the second electrical signal is applied to a cardiac branch on the opposite side of the body from the main vagal trunk to which the first electrical signal is applied. In one embodiment, the first electrical signal is applied to a left main trunk to minimize cardiac effects of the first electrical signal, and the second electrical signal is applied to a right cardiac branch, which modulates the sinoatrial node of the heart to maximize cardiac effects of the second electrical signal.

Figure 5:
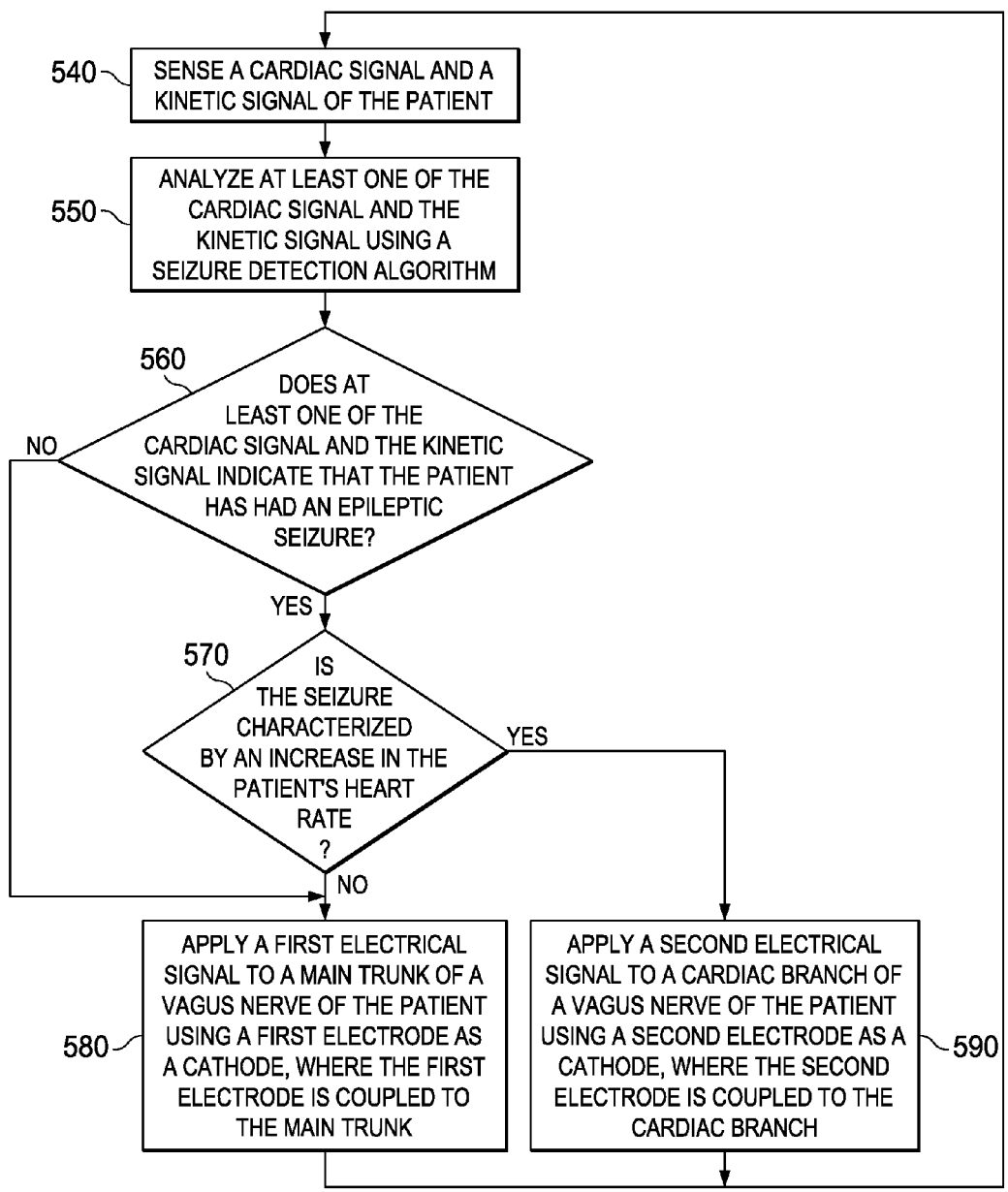
FIG. 5 illustrates a flowchart depiction of a method for providing first and second electrical signals to a main trunk and a cardiac branch of a vagus nerve, respectively, based upon whether or not at least one of a cardiac signal and a kinetic signal indicates that the patient has had an epileptic seizure, and whether the seizure is characterized by an increase in heart rate, in accordance with an illustrative embodiment of the present invention.

FIG. 5 is a flow diagram of another method of treating a patient having epilepsy according to the present invention. A sensor is used to sense a cardiac signal and a kinetic signal of the patient (540). In a particular embodiment, the cardiac sensor may comprise an electrode pair for sensing an ECG (electrocardiogram) or heart beat signal, and the kinetic signal may comprise a triaxial accelerometer to detect motion of at least a portion of the patient's body. The method further comprises analyzing at least one of the cardiac signal and the kinetic signal using seizure detection algorithm (550), and the output of the algorithm is used to determine whether at least one of the cardiac signal and the kinetic signal indicate that the patient has had an epileptic seizure (560).

If the patient has not had an epileptic seizure, the method comprises applying a first electrical signal to a main trunk of a vagus nerve of the patient using a first electrode, coupled to the main trunk, as a cathode (580). In one embodiment, the first electrical signal is an open-loop electrical signal having an on-time and off-time.

If the patient has had an epileptic seizure, a determination is made whether the seizure is characterized by an increase in the patient's heart rate (570). If the seizure is not characterized by an increase in the patient's heart rate, the method comprises applying the first electrical signal to the main trunk of a vagus nerve using the first electrode as a cathode (580). In one embodiment, the cathode comprises an upper main trunk electrode 125-1 and the anode is selected from a cardiac branch electrode 125-2 and a lower main trunk electrode 125-3. Conversely, if the seizure is characterized by an increase in the patient's heart rate, the method comprises applying a second electrical signal to a cardiac branch of a vagus nerve of the patient using a second electrode, coupled to the cardiac branch, as a cathode (590). The anode is an upper main trunk electrode 125-1 or a lower main trunk electrode 125-3. In one embodiment, the method may comprise suspending the first electrical and applying the second electrical signal.

The method then continues the sensing of the cardiac and kinetic signals of the patient (540) and resumes the method as outlined in FIG. 5.

Figure 6:
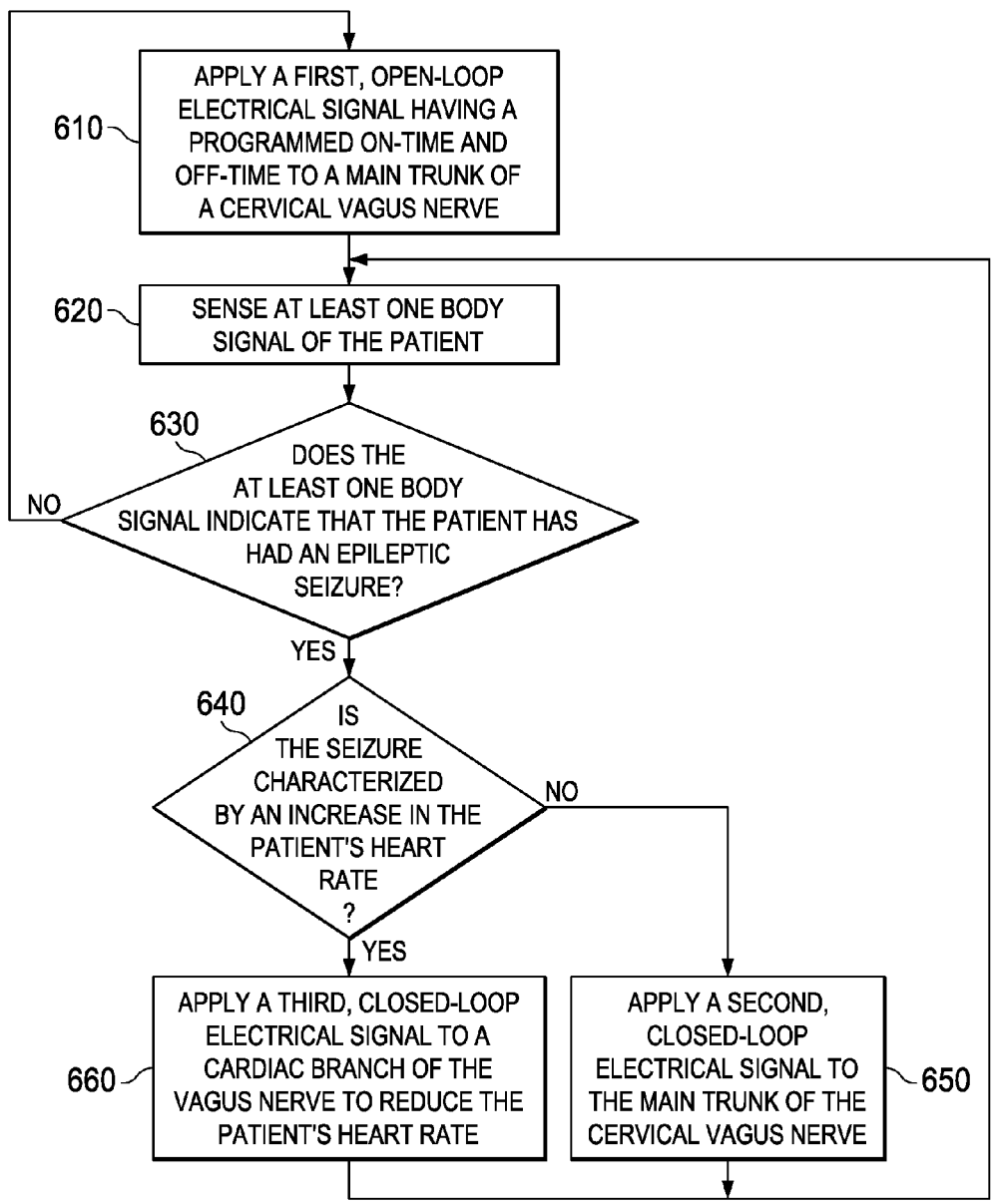
FIG. 6 illustrates a flowchart depiction of a method for providing a first, open-loop electrical signal to a main trunk of a vagus nerve, a second, closed-loop electrical signal to the main trunk of the vagus nerve based upon the patient having had an epileptic seizure not characterized by an increase in heart rate, and a third, closed-loop electrical signal to a cardiac branch of a vagus nerve based upon the patient having had an epileptic seizure characterized by an increase in heart rate, in accordance with an illustrative embodiment of the present invention.

FIG. 6 is a flow diagram of a further method of treating a patient having epilepsy according to the present invention. The method includes applying a first, open-loop electrical signal to a main trunk of a vagus nerve (610). The open-loop signal is characterized by an off-time in which electrical pulses are applied to the nerve, and an off-time in which electrical pulses are not applied to the nerve.

A sensor is used to sense at least one body signal of the patient (620), and a determination is made whether the at least one body signal indicates that the patient has had an epileptic seizure (630). If the patient has not had a seizure, the method continues applying the first, open-loop electrical signal to a main trunk of a vagus nerve (610). If the patient has had an epileptic seizure, a determination is made whether the seizure is characterized by an increase in the patient's heart rate (640). In one embodiment, the increase in heart rate is measured from a baseline heart rate existing prior to the seizure, e.g., a median heart rate for a prior period such as the 300 beats prior to the detection of the seizure event, or the 5 minutes prior to the detection of the seizure.

If the seizure is not characterized by an increase in the patient's heart rate, the method comprises applying a second, closed-loop electrical signal to the main trunk of the vagus nerve 650). In one embodiment, the second, closed-loop electrical signal is the same signal as the open-loop electrical signal, except that the second signal (as defined, e.g., by a current intensity, a pulse frequency, a pulse width and an on-time) is applied at a time different from the programmed timing of the first electrical signal. For example, if the first electrical signal comprises an on-time of 30 seconds and an off-time of 5 minutes, but a seizure is detected 1 minute after the end of a programmed on-time, the second electrical signal may comprise applying a 30 second pulse burst at the same current intensity, frequency, and pulse width as the first signal, but four minutes earlier than would have occurred absent the detected seizure. In another embodiment, the second, closed-loop electrical signal is a different signal than the first, open-loop electrical signal, and the method may also comprise suspending the first electrical before applying the second electrical signal. For example, the second, closed-loop electrical signal may comprise a higher current intensity, frequency, pulse width and/or on-time than the first, open-loop electrical signal, and may not comprise an off-time (e.g., the second electrical signal may be applied for a predetermined duration independent of the on-time of the first, open-loop electrical signal, such as a fixed duration of 1 minute, or may continue for as long as the body signal indicates the presence of the seizure event).

Returning to FIG. 6, if the seizure is characterized by an increase in the patient's heart rate, the method comprises applying a third, closed-loop electrical signal to a cardiac branch of a vagus nerve to reduce the patient's heart rate (660). The method may comprise suspending the first electrical as well as applying the third, closed-loop electrical signal. In one embodiment of the invention, each of the first, open-loop electrical signal, the second, closed-loop electrical signal, and the third, closed-loop electrical signal are applied unilaterally (i.e., to vagus nerve structures on the same side of the body) to the main trunk and cardiac branch of the vagus nerve. For example, the first, open-loop electrical signal and the second, closed-loop electrical signal may be applied to a left main trunk of the patient's cervical vagus nerve, and the third, closed-loop electrical signal may be applied to the left cardiac branch of the vagus nerve. Similarly, the first, second and third electrical signals may all be applied to the right vagus nerve of the patient. In alternative embodiments, one or more of the first, second and third electrical signals may be applied bilaterally, i.e., one of the first, second and third electrical signals is applied to a vagal structure on the opposite side of the body from the other two signals. For example, in a particular embodiment the first, open-loop signal and the second, closed-loop signal may be applied to a left main trunk of the patient's cervical vagus nerve, and the third, closed-loop electrical signal may be applied to a right cardiac branch of the patient's vagus nerve. Because the right cardiac branch modulates the sinoatrial node of the patient's heart, which is the heart's "natural pacemaker," the third electrical signal may have more pronounced effect in reducing the patient's heart rate if applied to the right cardiac branch.

After applying one of the second (650) and third (660) electrical signals to a vagus nerve of the patient, the method then continues sensing at least one body signal of the patient (620) and resumes the method as outlined in FIG. 6.

In the methods depicted in FIGS. 4-6, one or more of the parameters defining the first, second, and third electrical signals (e.g., number of pulses, pulse frequency, pulse width, On time, Off time, interpulse interval, number of pulses per burst, or interburst interval, among others) can be changed by a healthcare provided using a programmer 150.

Figure 7:
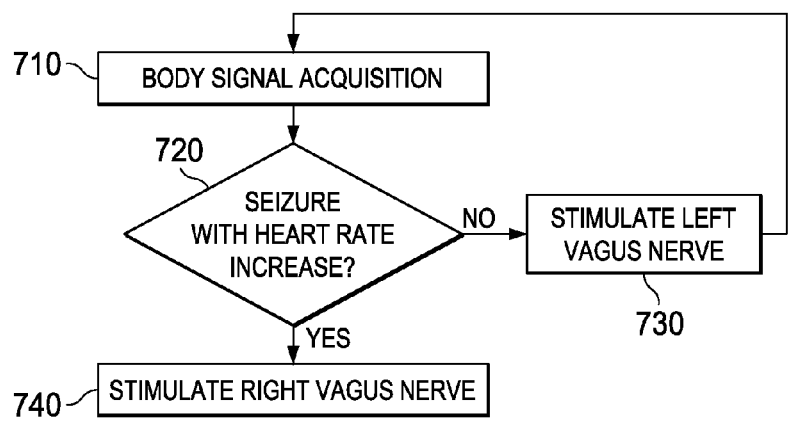
FIG. 7 is a flowchart depiction of a method for providing closed-loop vagus nerve stimulation for a patient with epilepsy by stimulating a right vagus nerve in response to detecting a seizure with tachycardia and stimulating a left vagus nerve in the absence of such a detection.

FIG. 7 is a flow diagram of a method of treating patients having seizures accompanied by increased heart rate. In one embodiment, tachycardia is defined as a neurogenic increase in heart rate, that is, an elevation in heart rate that occurs in the absence of motor activity or that if associated with motor activity, the magnitude of the increase in heart rate is larger than that caused by motor activity alone. In one embodiment, a body signal is acquired (710). The body signal may comprise one or more body signals that may be altered, changed or influenced by an epileptic seizure. As non-limiting examples, the body signal may comprise one or more of a cardiac signal such as heart rate, heart rate variability, or EKG complex morphology, a kinetic signal such as an accelerometer signal, a postural signal or body position signal), blood pressure, blood oxygen concentration, skin resistivity or conductivity, pupil dilation, eye movement, EEG, reaction time or other body signals. The body signal may be a real-time signal or a stored signal for delayed or later analysis. It may be acquired, for example, from a sensor element (e.g., coupled to a processor), from a storage device in which the signal data is stored.

The method further comprises determining whether or not the patient has had a seizure accompanied by an increase in heart rate (720). In one embodiment, the method comprises a seizure detection algorithm that analyzes the acquired body signal data and determines whether or not a seizure has occurred. In a particular embodiment, the method comprises an algorithm that analyzes one or more of a cardiac signal, a kinetic signal, a cognitive signal, blood pressure, blood oxygen concentration, skin resistivity or conductivity, pupil dilation, and eye movement to identify changes in the one or more signals that indicate a seizure has occurred. The method may comprise an output signal or data flag that may be asserted or set when the detection algorithm determines from the body signal(s) that the patient has had a seizure.

The method also comprises determining (720) whether or not the seizure is accompanied by an increase in heart rate. In one embodiment, the body data signal comprises a heart beat signal that may be analyzed to determine heart rate. In some embodiments, the heart beat signal may be used by the seizure detection algorithm to determine whether a seizure has occurred, while in other embodiments seizures are not detected using heart rate. Regardless of how the seizure is detected, however, the method of FIG. 7 comprises determining whether a detected seizure event is accompanied by an increase in heart rate. The increase may be determined in a variety of ways, such as by an increase in an instantaneous heart rate above a reference heart rate (which may be a predetermined interictal value such as 72 beats per minute (bpm), or a real-time measure of central tendency for a time window, such as a 5 minute median or moving average heart rate). Additional details about identifying increases in heart rate in the context of epileptic seizures are provided in U.S. Pat. Nos. 5,928,272, 6,341,236, 6,587,727, 6,671,556, 6,961, 618, 6,920,357, 7,457,665, as well as U.S. patent application Ser. Nos. 12/770,562, 12/771,727, 12/771,783, 12/884,051, 12/886,419, 12/896,525, 13/098,262, and 13/288,886, each of which is hereby incorporated by reference in its entirety herein.

If the body data signal does not indicate that the patient has had a seizure accompanied by tachycardia, the method comprises applying a first electrical signal to a left vagus nerve. If the body signal does indicate that the patient has experienced a seizure accompanied by tachycardia, the method comprises applying a second electrical signal to a right vagus nerve.

Without being bound by theory, it is believed that stimulation of the right vagus nerve, which enervates the right sinoatrial nerve that functions as the heart's natural pacemaker, will have a more prominent effect in slowing the heart rate than stimulation of the left vagus nerve. The present invention takes advantage of this electrical asymmetry of the left and right vagus nerves to minimize the effect of VNS on heart rate except where there is a need for acute intervention to slow the heart rate, i.e., when the patient has experienced and epileptic seizure, and the seizure is accompanied by an increase in heart rate. This may result in, for example, stimulation of the left vagus nerve either when there is no seizure (such as when an open-loop stimulation program off-time has elapsed and the program initiates stimulation in accordance with a programmed signal on-time), or when there is a detected seizure event that is not accompanied by an increase in heart rate (such as absence seizures); and stimulation of the right vagus nerve when there is a detected seizure event accompanied by a heart rate increase. In one embodiment, a programmed, open-loop electrical signal is applied to the left vagus nerve except when an algorithm analyzing the acquired body signal detects a seizure accompanied by a heart rate increase. In response to such a detection, a closed-loop electrical signal is applied to the right vagus nerve to slow the patient's (increased) heart rate. In some embodiments, the response to detecting a seizure accompanied by a heart rate increase may also include interrupting the application of the programmed-open-loop electrical signal to the left vagus nerve. The interrupted open-loop stimulation of the left vagus nerve may be resumed either when the seizure ends or the heart rate returns to a desired, lower heart rate.

In an additional embodiment of the invention, electrode pairs may be applied to each of the left and right vagus nerves of the patient, and used depending upon whether or not seizures accompanied by cardiac changes such as tachycardia are detected. In one such embodiment, a method of treating epilepsy patients may be provided as described below.

A method of treating a patient having epilepsy comprising:
coupling a first set of electrodes and a second set of electrodes to the vagi nerves of the patient, wherein said first electrode set is coupled to a main trunk of the left vagus nerve of the patient, and the second set of electrode is coupled to a main trunk of the right vagus nerve of the patient,
providing an electrical signal generator coupled to the first electrode set and the second electrode set,
receiving at least one body data stream,
analyzing the at least one body data stream using a seizure detection algorithm to determine
whether or not the patient has had an epileptic seizure,
applying a first electrical signal from the electrical signal generator to the main trunk of the left vagus nerve, based on a determination that the patient has had an epileptic seizure without cardiac changes, and
applying a second electrical signal from the electrical signal generator to the main trunk of the right vagus nerve, based on a determination that the patient has had an epileptic seizure.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A method of treating a patient having epilepsy via an implantable medical device which includes an electrical signal generator coupled to a first electrode and a second electrode where the first electrode is coupled to a main trunk of a vagus nerve of the patient and a second electrode is coupled to a cardiac branch of the vagus nerve of the patient, the method comprising:
receiving at least one body data stream;
analyzing the at least one body data stream using a seizure detection algorithm to determine an epileptic seizure state;
applying a first electrical signal from the electrical signal generator to the main trunk of the vagus nerve using the first electrode as a cathode, based on a determination that the epileptic seizure state of the patient is a first state where an epileptic seizure is not detected; and
applying a second electrical signal from the electrical signal generator to the cardiac branch of the vagus nerve using the second electrode as the cathode, based on a determination that the epileptic seizure state of the patient is a second state where the epileptic seizure is detected.

2. The method of claim 1, wherein the second electrical signal is configured to reduce a heart rate of the patient.

3. The method of claim 1, wherein applying the first electrical signal is based on a programmed duty cycle having at least a programmed on-time and a programmed off-time.

4. The method of claim 1, wherein based on the determination that the epileptic seizure state of the patient is the second state where the epileptic seizure is detected, the method further comprises identifying an increase in a patient's heart rate, and applying the second electrical signal to reduce the patient's heart rate.

5. The method of claim 4, further comprising:
sensing the patient's heart rate in response to applying the second electrical signal, and interrupting the second electrical signal if a decrease in the patient's heart rate reaches a lower heart rate threshold.

6. The method of claim 4 further comprising:
sensing the patient's heart rate in response to applying the second electrical signal, and modifying the second electrical signal to maintain the patient's heart rate between an upper rate threshold and the lower heart rate threshold.

7. The method of claim 1 wherein the first electrode is proximal to a brain of the patient relative to the second electrode, wherein applying the first electrical signal comprises using the first electrode as the cathode and the second electrode as an anode, and wherein applying the second electrical signal comprises using the second electrode as the cathode and first electrode as the anode to reduce a patient's heart rate.

8. The method of claim 7, wherein the implantable medical device includes a polarity reversal unit capable of reversing a polarity of the first electrode and the second electrode to apply the first electrical signal and the second electrical signal.

9. The method of claim 1, wherein the implantable medical device includes a third electrode coupled to the main trunk of the vagus nerve and to a programmable signal generator,
wherein applying the first electrical signal comprises applying the first electrical signal to the vagus nerve using the first electrode as the cathode and the third electrode as an anode.

10. The method of claim 1, wherein at least one of the first electrical signal and the second electrical signal is a microburst electrical signal characterized by having a number of pulses per microburst from 2 pulses to about 25 pulses, an interpulse interval of about 2 msec to about 50 msec, an interburst period of at least 100 msec, and a microburst duration of less than about 1 sec.

11. The method of claim 1, wherein based on the determination that the epileptic seizure state of the patient is the second state where the epileptic seizure is detected, the method further comprises identifying an increase in a patient's heart rate and applying both:
the first electrical signal from the electrical signal generator to the main trunk of the vagus nerve using the first electrode as the cathode, and
the second electrical signal from the electrical signal generator to the cardiac branch of the vagus nerve using the second electrode as the cathode.

12. The method of claim 11, wherein the first electrical signal and the second electrical signal are applied to the vagus nerve in at least one of a sequential fashion, a simultaneous fashion, and in alternating and repeating fashion.

13. A method of treating a patient having epilepsy comprising:
sensing a cardiac signal and a kinetic signal of the patient;
analyzing at least one of the cardiac signal and the kinetic signal;
determining whether or not the patient has had an epileptic seizure based on the analyzing;
in response to a determination that the patient has had the epileptic seizure, determining whether or not the epileptic seizure is characterized by an increase in a patient's heart rate;
applying a first electrical signal to a main trunk of a vagus nerve of the patient using a first electrode as a cathode based on one of: a) a determination that the patient has not had the epileptic seizure, and b) a determination that the patient has had the epileptic seizure that is not characterized by the increase in the patient's heart rate, wherein the first electrode is coupled to the main trunk; and
applying a second electrical signal to a cardiac branch of the vagus nerve of the patient using a second electrode as the cathode based on a determination that the patient has had the epileptic seizure characterized by the increase in the patient's heart rate, wherein the second electrode is coupled to the cardiac branch.

14. The method of claim 13, wherein applying the first electrical signal is based on a programmed duty cycle having at least a programmed on-time and a programmed off-time.

15. The method of claim 13, wherein the second electrical signal is configured to reduce the patient's heart rate.

16. The method of claim 13 further comprising:
applying the first electrical signal comprises using the first electrode as the cathode and the second electrode as an anode; and
applying the second electrical signal comprises using the second electrode as the cathode and the first electrode as the anode;
wherein the first electrode is proximal to a brain of the patient relative to the second electrode.

17. The method of claim 16 further comprising utilizing a polarity reversal unit capable of reversing a polarity of the first electrode and the second electrode to apply the first electrical signal and the second electrical signal.

18. The method of claim 17 further comprising:
applying the first electrical signal at a first point in time based on a determination that the patient has not had the epileptic seizure characterized by the increase in the patient's heart rate,
reversing the polarity of the first electrode and the second electrode, and
applying the second electrical signal at a second point in time based on a determination that the patient has had the epileptic seizure characterized by the increase in the patient's heart rate.

19. A method of treating a patient having epilepsy comprising:
applying a first electrical signal to a main trunk of a vagus nerve of the patient, wherein the first electrical signal is an open-loop electrical signal having a programmed on-time and a programmed off-time;
sensing at least one body signal of the patient, determining a start of an epileptic seizure based on the at least one body signal, determining whether or not the epileptic seizure is characterized by an increase in a patient's heart rate;
applying a second, closed-loop electrical signal to the main trunk of the vagus nerve based on a determination that the epileptic seizure is not characterized by the increase in the patient's heart rate; and
applying a third, closed-loop electrical signal to a cardiac branch of the vagus nerve based on a determination that the epileptic seizure is characterized by the increase in the patient's heart rate, wherein the third electrical signal is applied to reduce the patient's heart rate.

20. A method of treating a patient having epilepsy comprising:
sensing at least one body signal of the patient;
determining whether or not the patient has had an epileptic seizure based on the at least one body signal;
sensing a cardiac signal of the patient;
in response to a determination that the patient has had the epileptic seizure, determining whether or not the epileptic seizure is characterized by an increase in a patient's heart rate;
applying a first electrical signal to a left vagus nerve of the patient using a first electrode as a cathode based on one of a) a determination that the patient has not had the epileptic seizure, and b) a determination that the patient has had the epileptic seizure that is not characterized by the increase in the patient's heart rate, wherein the first electrode is coupled to the left vagus nerve; and
applying a second electrical signal to a right vagus nerve of the patient using a second electrode as the cathode based on a determination that the patient has had the epileptic seizure characterized by the increase in the patient's heart rate, wherein the second electrode is coupled to the right vagus nerve.

* * * * *